(12) United States Patent
Schoenefeld

(10) Patent No.: US 7,643,862 B2
(45) Date of Patent: *Jan. 5, 2010

(54) VIRTUAL MOUSE FOR USE IN SURGICAL NAVIGATION

(75) Inventor: Ryan Schoenefeld, Fort Wayne, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 525 days.

This patent is subject to a terminal disclaimer.

(21) Appl. No.: 11/434,035

(22) Filed: May 15, 2006

(65) Prior Publication Data

US 2007/0073137 A1    Mar. 29, 2007

Related U.S. Application Data

(63) Continuation-in-part of application No. 11/227,741, filed on Sep. 15, 2005, now abandoned.

(51) Int. Cl.
    *A61B 5/05*      (2006.01)

(52) U.S. Cl. ...................... 600/407; 600/414; 600/426

(58) Field of Classification Search ................ 600/407, 600/408, 429, 416; 382/128; 606/130; 345/156
See application file for complete search history.

(56) References Cited

U.S. PATENT DOCUMENTS

| | | | |
|---|---|---|---|
| 3,541,541 A | 11/1970 | Engelbart | |
| 4,341,220 A | 7/1982 | Perry | |
| 4,360,028 A | 11/1982 | Barbier et al. | |
| 4,583,538 A | 4/1986 | Onik et al. | |
| 4,791,934 A | 12/1988 | Brunnett | |
| 4,945,914 A | 8/1990 | Allen | |
| 4,991,579 A | 2/1991 | Allen | |
| 5,016,639 A | 5/1991 | Allen | |
| 5,094,241 A | 3/1992 | Allen | |
| 5,097,839 A | 3/1992 | Allen | |

(Continued)

FOREIGN PATENT DOCUMENTS

EP      0 427 358 A1      5/1991

(Continued)

OTHER PUBLICATIONS

Visarius, H., et al., Man-Machine Interfaces in Computer Assisted Surgery, Computer Aided Surgery, 1997, vol. 2, p. 102-107.
Langlotz, F., et al., Femoral Stem navigation with the SurgiGATE System, Navigation and Robotics in Total Joint and Spine Surgery, 2004, Springer, Chapter 13, p. 102-109.
Muller PE, Pellengahr C, Witt M, Kircher J, Reflor HJ, Jansson V. Influence of minimally invasive surgery on implant positioning and the functional outcome for medial unicompartmental knee arthroplasty. J Arthroplasty 2004; 19(3): 296-301.
DiGioia AM, Jaramaz B; Colgan BD. Computer assisted orthopaedic surgery. Image guided and robotic assistive technologies. Clin Orthop Sep. 1998;(354):8-16.

(Continued)

*Primary Examiner*—Eric F Winakur
*Assistant Examiner*—Helene Bor
(74) *Attorney, Agent, or Firm*—Bose McKinney & Evans LLP

(57) ABSTRACT

A method of performing a surgery is provided including a surgical navigation system having a tracking system, computer and monitor placed outside of a sterile field. An input pad and a tracking array attachable to a surgical instrument or bone are placed into the sterile field along with a probe having a probe array. The tracking array and the probe array are acquired by the tracking system and a virtual mouse is activated by positioning the probe relative to the input pad, thereby causing a mouse input to the computer with the virtual mouse.

25 Claims, 18 Drawing Sheets

U.S. PATENT DOCUMENTS

| | | |
|---|---|---|
| 5,119,817 A | 6/1992 | Allen |
| 5,142,930 A | 9/1992 | Allen et al. |
| 5,178,164 A | 1/1993 | Allen |
| 5,182,641 A | 1/1993 | Diner et al. |
| 5,211,164 A | 5/1993 | Allen |
| 5,222,499 A | 6/1993 | Allen et al. |
| 5,230,338 A | 7/1993 | Allen et al. |
| 5,230,623 A | 7/1993 | Guthrie et al. |
| 5,309,913 A | 5/1994 | Kormos et al. |
| 5,383,454 A | 1/1995 | Bucholz |
| 5,389,101 A | 2/1995 | Heilbrun et al. |
| 5,397,329 A | 3/1995 | Allen |
| 5,517,990 A | 5/1996 | Kalfas et al. |
| 5,603,318 A | 2/1997 | Heilbrun et al. |
| 5,628,315 A | 5/1997 | Vilsmeier et al. |
| 5,631,973 A | 5/1997 | Green |
| 5,682,886 A | 11/1997 | Delp et al. |
| 5,682,890 A | 11/1997 | Kormos et al. |
| 5,732,703 A | 3/1998 | Kalfas et al. |
| 5,769,861 A | 6/1998 | Vilsmeier |
| 5,772,594 A | 6/1998 | Barrick |
| 5,776,064 A | 7/1998 | Kalfas et al. |
| 5,799,055 A | 8/1998 | Peshkin et al. |
| 5,835,791 A | 11/1998 | Goff et al. |
| 5,836,954 A | 11/1998 | Heilbrun et al. |
| 5,851,183 A | 12/1998 | Bucholz |
| 5,871,018 A | 2/1999 | Delp et al. |
| 5,902,239 A | 5/1999 | Buurman |
| 5,967,982 A | 10/1999 | Barnett |
| 5,980,535 A | 11/1999 | Barnett et al. |
| 5,987,960 A | 11/1999 | Messner et al. |
| 5,999,837 A | 12/1999 | Messner et al. |
| 6,021,343 A | 2/2000 | Foley et al. |
| 6,069,932 A | 5/2000 | Peshkin et al. |
| 6,122,541 A | 9/2000 | Cosman et al. |
| 6,167,145 A | 12/2000 | Foley et al. |
| 6,178,345 B1 | 1/2001 | Vilsmeier et al. |
| 6,190,395 B1 | 2/2001 | Williams |
| 6,198,794 B1 | 3/2001 | Peshkin et al. |
| 6,205,411 B1 | 3/2001 | DiGioia, III et al. |
| 6,235,038 B1 | 5/2001 | Hunter et al. |
| 6,236,875 B1 | 5/2001 | Bucholz et al. |
| 6,246,898 B1 * | 6/2001 | Vesely et al. ................. 600/424 |
| 6,285,902 B1 | 9/2001 | Kienzle, III et al. |
| 6,306,126 B1 | 10/2001 | Moctezuma |
| 6,377,839 B1 | 4/2002 | Kalfas et al. |
| 6,379,302 B1 | 4/2002 | Kessman et al. |
| 6,381,485 B1 | 4/2002 | Hunter et al. |
| 6,402,762 B2 | 6/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,434,507 B1 | 8/2002 | Clayton et al. |
| 6,470,207 B1 | 10/2002 | Simon et al. |
| 6,490,467 B1 | 12/2002 | Bucholz et al. |
| 6,491,699 B1 | 12/2002 | Henderson et al. |
| 6,527,443 B1 | 3/2003 | Vilsmeier et al. |
| 6,535,756 B1 | 3/2003 | Simon et al. |
| 6,553,152 B1 | 4/2003 | Miller et al. |
| 6,584,174 B2 | 6/2003 | Schubert et al. |
| 6,609,022 B2 | 8/2003 | Vilsmeier et al. |
| 6,674,916 B1 | 1/2004 | Deman et al. |
| 6,697,664 B2 | 2/2004 | Kienzle, III et al. |
| 6,714,629 B2 | 3/2004 | Vilsmeier |
| 6,721,178 B1 * | 4/2004 | Clark et al. ................. 361/686 |
| 6,724,922 B1 | 4/2004 | Vilsmeier |
| 6,725,080 B2 | 4/2004 | Melkent et al. |
| 6,725,082 B2 | 4/2004 | Sati et al. |
| 6,754,374 B1 | 6/2004 | Miller et al. |
| 6,772,002 B2 | 8/2004 | Schmidt et al. |
| 6,776,526 B2 | 8/2004 | Zeiss |
| 6,782,287 B2 | 8/2004 | Grzeszczuk et al. |
| 6,856,826 B2 | 2/2005 | Seeley et al. |
| 6,856,827 B2 | 2/2005 | Seeley et al. |
| 6,856,828 B2 | 2/2005 | Cossette et al. |
| 6,887,245 B2 | 5/2005 | Kienzle, III et al. |
| 6,887,247 B1 | 5/2005 | Couture et al. |
| 6,892,088 B2 | 5/2005 | Faulkner et al. |
| 6,895,268 B1 | 5/2005 | Rahn et al. |
| 6,896,657 B2 | 5/2005 | Willis |
| 6,917,827 B2 | 7/2005 | Kienzle, III |
| 6,920,347 B2 | 7/2005 | Simon et al. |
| 6,925,339 B2 | 8/2005 | Grimm et al. |
| 6,926,673 B2 | 8/2005 | Roberts et al. |
| 6,932,823 B2 | 8/2005 | Grimm et al. |
| 6,947,582 B1 | 9/2005 | Vilsmeier et al. |
| 6,947,783 B2 | 9/2005 | Immerz |
| 6,950,689 B1 | 9/2005 | Willis et al. |
| 6,978,166 B2 | 12/2005 | Foley et al. |
| 6,988,009 B2 | 1/2006 | Grimm et al. |
| 6,990,220 B2 | 1/2006 | Ellis et al. |
| 7,008,430 B2 | 3/2006 | Dong et al. |
| 7,010,095 B2 | 3/2006 | Mitschke et al. |
| 7,274,290 B2 * | 9/2007 | Morita et al. ................ 340/539.12 |
| 2001/0007918 A1 | 7/2001 | Vilsmeier et al. |
| 2001/0011175 A1 | 8/2001 | Hunter et al. |
| 2001/0036245 A1 | 11/2001 | Kienzle, III et al. |
| 2001/0051881 A1 * | 12/2001 | Filler ................................ 705/3 |
| 2002/0077540 A1 | 6/2002 | Kienzle, III |
| 2002/0095081 A1 | 7/2002 | Vilsmeier |
| 2002/0183610 A1 | 12/2002 | Foley et al. |
| 2003/0059097 A1 | 3/2003 | Abovitz et al. |
| 2003/0071893 A1 | 4/2003 | Miller et al. |
| 2003/0209096 A1 | 11/2003 | Pandey et al. |
| 2004/0015077 A1 | 1/2004 | Sati et al. |
| 2004/0030245 A1 | 2/2004 | Noble et al. |
| 2004/0087852 A1 | 5/2004 | Chen et al. |
| 2004/0097952 A1 | 5/2004 | Sarin et al. |
| 2004/0127788 A1 | 7/2004 | Arata |
| 2004/0141015 A1 | 7/2004 | Fitzmaurice et al. |
| 2004/0169673 A1 | 9/2004 | Crampe et al. |
| 2004/0254454 A1 | 12/2004 | Kockro |
| 2004/0267242 A1 | 12/2004 | Grimm et al. |
| 2005/0015003 A1 | 1/2005 | Lachner et al. |
| 2005/0015005 A1 | 1/2005 | Kockro |
| 2005/0015022 A1 | 1/2005 | Richard et al. |
| 2005/0015099 A1 | 1/2005 | Momoi et al. |
| 2005/0020909 A1 | 1/2005 | Moctezuma de la Barrera et al. |
| 2005/0020911 A1 | 1/2005 | Viswanathan et al. |
| 2005/0021037 A1 | 1/2005 | McCombs et al. |
| 2005/0021039 A1 | 1/2005 | Cusick et al. |
| 2005/0021043 A1 | 1/2005 | Jansen et al. |
| 2005/0021044 A1 | 1/2005 | Stone et al. |
| 2005/0024323 A1 | 2/2005 | Salazar-Ferrer et al. |
| 2005/0033117 A1 | 2/2005 | Ozaki et al. |
| 2005/0033149 A1 | 2/2005 | Strommer et al. |
| 2005/0038337 A1 | 2/2005 | Edwards |
| 2005/0049477 A1 | 3/2005 | Fu et al. |
| 2005/0049478 A1 | 3/2005 | Kuduvalli et al. |
| 2005/0049485 A1 | 3/2005 | Harmon et al. |
| 2005/0049486 A1 | 3/2005 | Urquhart et al. |
| 2005/0054915 A1 | 3/2005 | Sukovic et al. |
| 2005/0054916 A1 | 3/2005 | Mostafavi |
| 2005/0059873 A1 | 3/2005 | Glozman et al. |
| 2005/0075632 A1 | 4/2005 | Russell et al. |
| 2005/0080334 A1 | 4/2005 | Willis |
| 2005/0085714 A1 | 4/2005 | Foley et al. |
| 2005/0085715 A1 | 4/2005 | Dukesherer et al. |
| 2005/0085717 A1 | 4/2005 | Shahidi |
| 2005/0085718 A1 | 4/2005 | Shahidi |
| 2005/0085720 A1 | 4/2005 | Jascob et al. |
| 2005/0090730 A1 | 4/2005 | Cortinovis et al. |
| 2005/0090733 A1 | 4/2005 | Van Der Lugt et al. |
| 2005/0096515 A1 | 5/2005 | Geng |

| | | |
|---|---|---|
| 2005/0096535 A1 | 5/2005 | de la Barrera |
| 2005/0101970 A1 | 5/2005 | Rosenberg |
| 2005/0113659 A1 | 5/2005 | Pothier et al. |
| 2005/0113960 A1 | 5/2005 | Karau et al. |
| 2005/0119561 A1 | 6/2005 | Kienzle, III |
| 2005/0119565 A1 | 6/2005 | Pescatore |
| 2005/0119639 A1 | 6/2005 | McCombs et al. |
| 2005/0119783 A1 | 6/2005 | Brisson et al. |
| 2005/0124988 A1 | 6/2005 | Terrill-Grisoni et al. |
| 2005/0137599 A1 | 6/2005 | Masini |
| 2005/0148850 A1 | 7/2005 | Lahm et al. |
| 2005/0148855 A1 | 7/2005 | Kienzle, III |
| 2005/0197568 A1 | 9/2005 | Vass et al. |
| 2005/0197569 A1 | 9/2005 | McCombs |
| 2005/0203373 A1 | 9/2005 | Boese et al. |
| 2005/0203374 A1 | 9/2005 | Vilsmeier |
| 2005/0203375 A1 | 9/2005 | Willis et al. |
| 2005/0203383 A1 | 9/2005 | Moctezuma de la Barrera et al. |
| 2005/0203384 A1 | 9/2005 | Sati et al. |
| 2005/0215879 A1 | 9/2005 | Chuanggui |
| 2005/0215888 A1 | 9/2005 | Grimm et al. |
| 2005/0216032 A1 | 9/2005 | Hayden |
| 2005/0228250 A1 | 10/2005 | Bitter et al. |
| 2005/0228266 A1 | 10/2005 | McCombs |
| 2005/0228270 A1 | 10/2005 | Lloyd et al. |
| 2005/0228404 A1 | 10/2005 | Vandevelde |
| 2005/0234335 A1 | 10/2005 | Simon et al. |
| 2005/0234465 A1 | 10/2005 | McCombs et al. |
| 2005/0251030 A1 | 11/2005 | Azar et al. |
| 2005/0267353 A1 | 12/2005 | Marquart et al. |
| 2005/0267354 A1 | 12/2005 | Marquart et al. |
| 2005/0267358 A1 | 12/2005 | Tuma et al. |
| 2005/0267360 A1 | 12/2005 | Birkenbach et al. |
| 2005/0267365 A1 | 12/2005 | Sokulin et al. |
| 2005/0267722 A1 | 12/2005 | Marquart et al. |
| 2005/0277832 A1 | 12/2005 | Foley et al. |
| 2005/0279368 A1 | 12/2005 | McCombs |
| 2005/0281465 A1 | 12/2005 | Marquart et al. |
| 2005/0288575 A1 | 12/2005 | de la Barrera et al. |
| 2005/0288578 A1 | 12/2005 | Durlak |
| 2006/0004284 A1 | 1/2006 | Grunschlager et al. |
| 2006/0009780 A1 | 1/2006 | Foley et al. |
| 2006/0015018 A1 | 1/2006 | Jutras et al. |
| 2006/0015030 A1 | 1/2006 | Poulin et al. |
| 2006/0025677 A1 | 2/2006 | Verard et al. |
| 2006/0025679 A1 | 2/2006 | Viswanathan et al. |
| 2006/0025681 A1 | 2/2006 | Abovitz et al. |
| 2006/0036149 A1 | 2/2006 | Lavigna et al. |
| 2006/0036151 A1 | 2/2006 | Ferre et al. |
| 2006/0036162 A1 | 2/2006 | Shahidi et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0052691 A1 | 3/2006 | Hall et al. |
| 2006/0058604 A1 | 3/2006 | Avinash et al. |
| 2006/0058615 A1 | 3/2006 | Mahajan et al. |
| 2006/0058616 A1 | 3/2006 | Marquart et al. |
| 2006/0058644 A1 | 3/2006 | Hoppe et al. |
| 2006/0058646 A1 | 3/2006 | Viswanathan |
| 2006/0058663 A1 | 3/2006 | Willis et al. |
| 2006/0209030 A1* | 9/2006 | Morita et al. ............ 345/168 |
| 2006/0251026 A1 | 11/2006 | Stone |

FOREIGN PATENT DOCUMENTS

| | | | |
|---|---|---|---|
| EP | 0 649 117 A2 | | 4/1995 |
| EP | 0 832 609 A2 | | 4/1998 |
| EP | 0 904 735 A2 | | 3/1999 |
| EP | 1 226 788 A1 | | 7/2002 |
| GB | 2 246 936 | | 2/1992 |
| WO | WO 0154558 A2 | * | 8/2001 |
| WO | WO 02/35454 A1 | | 5/2002 |
| WO | WO 02/62248 A1 | | 6/2002 |
| WO | WO 02/067783 A2 | | 9/2002 |
| WO | WO 04/001569 A2 | | 12/2003 |
| WO | WO 2004/006770 A2 | | 1/2004 |
| WO | WO 2004/069036 A2 | | 8/2004 |
| WO | WO 2004/069040 A2 | | 8/2004 |

OTHER PUBLICATIONS

David Stulberg S. How accurate is current TKR instrumentation? Clin Orthop. Nov. 2003;(416):177-84.

Bathis H, Perlick L, Tingart M, Luring C, Zurakowski D, Grifka J. Alignment in total knee arthroplasty. A comparison of computer-assisted surgery with the conventional technique. J Bone Joint Surg Br. 2004;86(5):682-687.

Chauhan SK, Clark GW, Lloyd S, Scott RG, Breidhal W, Sikorski JM. Computer-assisted total knee replacement: a controlled cadaver study using a multi-parameter quantitative CT assessment of alignment (the Perth CT Protocol). J Bone Joint Surg [Br] 2004;86-B:818-23.

James B. Stiehl et al., Navigation and Robotics in Total Joint and Spine Surgery, Chapter 3 C-Arm-Based Navigation, Springer-Verlag (2004) (9 pages).

"Acumen™ Surgical Navigation System, Surgical Navigation Applications" (2003) (2 pages).

Acumen™ Surgical Navigation System, Understanding Surgical Navigation (2003) (2 pages).

James B. Stiehl et al. Navigation and Robotics in Total Joint and Spine Surgery, Chapter 1 Basics of Computer-Assisted Orthopedic Surgery (CAOS), Springer-Verlag (2004) (9 pages).

Donald G. Eckhoff, Joel M. Bach, Victor M. Spitzer, Karl D. Reinig, Michelle M. Bagur, Todd H. Baldini, David Rubinstein, and Stephen Humphries, "Three-Dimensional Morphology and Kinematics of the Distal Part of the Femur Viewed in Virtual Reality. Part II," J Bone Joint Surg. Am 2003 85(Supp 4): 97-104.

"Real-Time Image Segmentation for Image-Guided Surgery" by Warfield, Simon; 14 pages; http://splweb.bwh.harvard.edu:8000/pages/papers/warfield/sc98/; accepted to appear at SC98.

"A Computer-Assisted Total Knee Replacement Surgical System Using a Calibrated Robot," Thomas C. Kienzle III, S. David Stulburg, Michael Peshkin, Arthur Quaid, Jon Lea, Ambarish Goswami, and Chi-Haur Wu, in "Computer-Integrated Surgery: Technology and Clinical Applications," ed. Russell H. Taylor, et. al., 1996 MIT Press. (28 pages).

Luck, J.F., Debrunner, C., Hoff, W., He, Q., and Small, D. "Development and Analysis of a Real-Time Human Motion Tracking System," in *Proc. of Workshop on Applications of Computer Vision*. 2002. Orlando, FL, IEEE (7 pages).

DiFranco, D.E. et al., "Recovery of 3D Articulated Motion from 2D Correspondences," Cambridge Research Laboratory Technical Report CRL 99/7, Dec. 1999 (20 pages).

Traxtal Technologies—Virtual Keypad, (printed May 23, 2005) pp. 1-2, http://www.traxtal.com/products/products_input_virtualkeypad.htm?print.

C. Graetzel, T.W. Fong, S. Grange, and C. Baur, "A non-contact mouse for surgeon-computer interaction," Technology and Health Care, vol. 12, No. 3, 2004, pp. 245-257.

Habets, R.J.E.: *Computer assistance in orthopaedic surgery*. Promoters: prof.dr.ir. A. Hasman, prof.dr.ir. F.A. Gerritsen; copromoter: dr.ir. J.A. Blom. Technische Universiteit Eindhoven, ISBN 90-386-1940-5, Nov. 4, 2002. (4 pages).

Visarius H, Gong J, Scheer C, Haralamb S, Nolte LP, Man-machine interfaces in computer assisted surgery. Comput Aid Surg 1997;2:102-107.

* cited by examiner

VIRTUAL MOUSE FOR USE IN SURGICAL NAVIGATION

RELATED APPLICATIONS

This application is a continuation-in-part of U.S. patent application Ser. No. 11/227,741, filed Sep. 15, 2005 now abandoned, the disclosure of which is hereby incorporated by reference in its entirety.

FIELD OF THE INVENTION

The present teachings relate generally to surgical navigation and more particularly to a method of using a virtual input device with a surgical navigation procedure.

BACKGROUND

Surgical navigation systems, also known as computer assisted surgery and image guided surgery, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such as fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical navigation procedure, surgeons often utilize "tracking arrays" that are coupled to the surgical components. The tracking arrays allow the surgeon to accurately track the location of these surgical components, as well as the patient's bones during the surgery. By knowing the physical location of the tracking array, the software detection program of the tracking system is able to calculate the position of the tracked component relative to a surgical plan image.

It is known to employ a keypad on the back of a universal calibrator used in a surgical navigation procedure. This "virtual keypad" allows the user to access certain system functions from the sterile field without using the touch screen or mouse, the latter items being located outside of the sterile field. The enabled functions of this known virtual keypad vary depending on application, but are accessed in the same manner. The user touches the desired button on the virtual keypad using the tip of a calibrated probe (or calibrated drill guide). The array of the universal calibrator and the probe array (or drill guide array) must be in view of the camera to enable the virtual keypad function.

The known virtual keypad is limited in the number of tasks that are pre-programmed into the software, as well as requires the incorporation and use of additional instrumentation during the surgical procedure. Thus, it would be desirable to overcome these and other shortcomings of the prior art.

SUMMARY OF THE INVENTION

The present teachings provide an apparatus and methods for using a probe, tracking array or other surgical instrument tracked during a surgical navigation procedure as a virtual mouse or its functional equivalent.

In one form thereof, there is provided a method of performing a surgery including a surgical navigation system having a tracking system, computer and monitor placed outside of a sterile field. An input pad and a tracking array attachable to a surgical instrument or bone are placed into the sterile field along with a probe having a probe array. The tracking array and the probe array are acquired by the tracking system and a virtual mouse is activated by positioning the probe relative to the input pad, thereby causing a mouse input to the computer with the virtual mouse.

In another form thereof, there is provided a surgical navigation system. This system includes a computer having a monitor and surgical navigation utilities software, a tracking system coupled to the computer and establishing a measurement field, a tracking array attachable to a surgical instrument or a bone, an input pad associated with the tracking array, and a probe having a probe array. The tracking array and probe array are each recognizable by the tracking system when exposed to the measurement field. The software comprises a program that when executed causes the system to recognize positioning of the probe relative to the input pad as a mouse input.

In certain exemplary embodiments, the input pad is located on the tracking array and comprises one or more pad markers and/or a substantially flat surface configured to cooperate with a probe to cause the mouse input to the computer. According to these exemplary embodiments, the mouse input is generated when a tip of the probe is positioned substantially near one of the pad markers or moved along the substantially flat surface of the input pad.

In other exemplary embodiments, the tip of the probe can be moved away from the pad marker or the substantially flat surface to cause a second mouse input to the computer. In yet other exemplary embodiments, the probe array can be occluded from exposure to the measurement field to cause the second mouse input. According to these exemplary embodiments, the first mouse input could be interpreted by the computer as representing a single click of a conventional mouse that identifies a function on the computer monitor with a conventional mouse pointer. Moreover, the second mouse input could be interpreted by the computer as representing a double click of the conventional mouse wherein the function identified by the first mouse input is selected or activated. In other exemplary embodiments, the first and/or second mouse inputs may also be interpreted as other known mouse inputs, such as scrolling a menu or manipulating an object on the computer monitor.

BRIEF DESCRIPTION OF DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
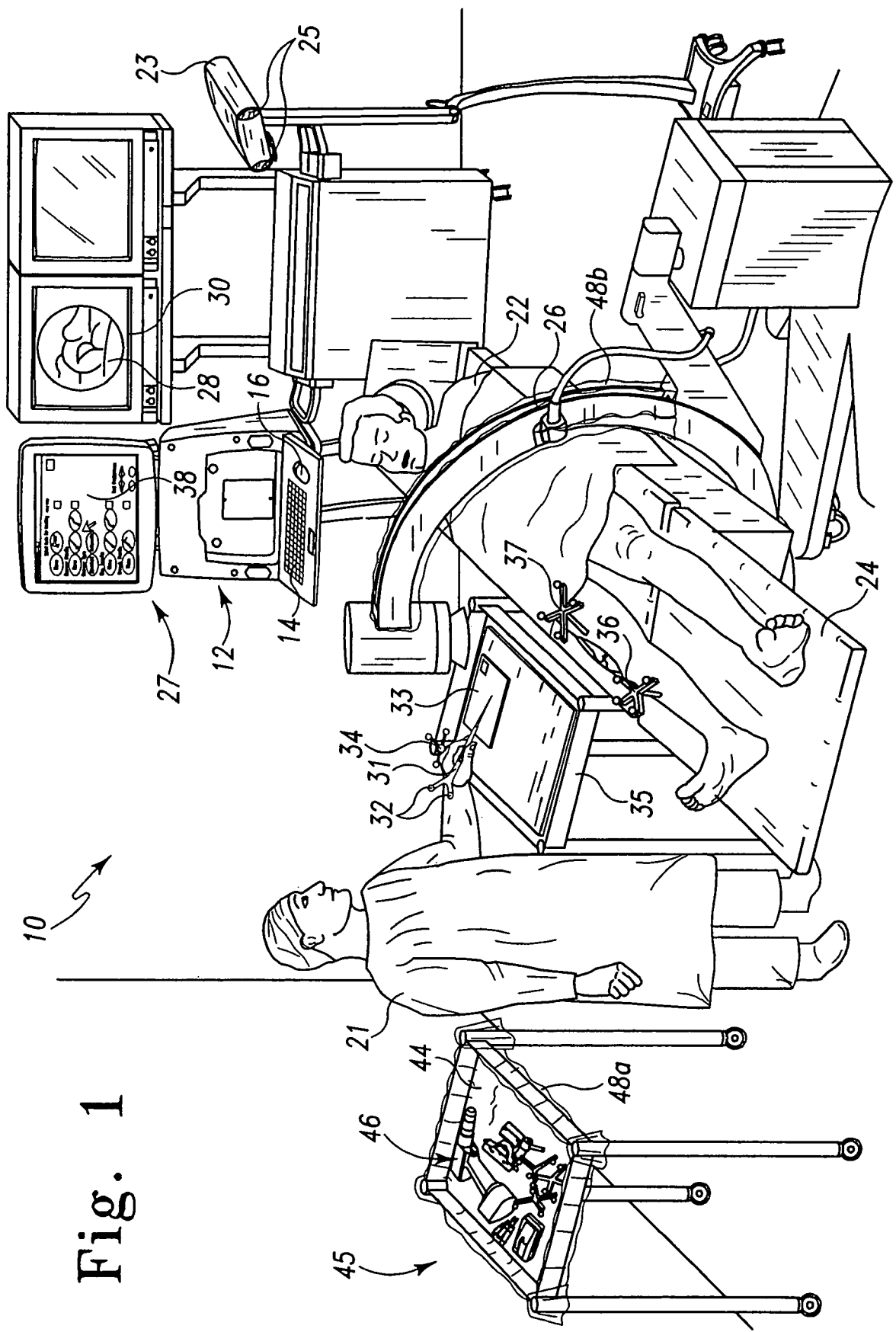
FIG. 1 is a perspective view of an operating room setup in a surgical navigation embodiment in accordance with the present teachings.

FIG. 1 shows a perspective view of an operating room with surgical navigation system 10. System 10 may include one or more computers 12 which may be operated by a keyboard 14 and a conventional or physical mouse 16, all of which may be located outside the sterile field. Physician or surgeon 21 is aided by the surgical navigation system in performing knee arthroplasty, also known as knee replacement surgery, on patient 22 shown lying on operating table 24. Surgical navigation system 10 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as C-arm fluoroscope 26 with fluoroscope display image 28 to show a real-time image of the patient's knee on monitor 30. Physician 21 uses surgical probe 31 to reference a point on the patient's knee, and reference arrays 36 and 37, attached to the patient's femur and tibia to provide known anatomic reference points so the surgical navigation system can compensate for leg movement.

In addition, as illustrated here, physician 21 may use probe 31, having markers 32, as a virtual mouse in combination with an input pad or touch pad 33 and a locating array 34. The pad 33 and locating array 34 may be supported by a stand or table 35 or other suitable structure for support within reach of the surgeon 21. A display image or user interface screen 38 displayed on display 27 includes a plurality of icons for selection by the physician 21 through use of the virtual mouse. The virtual mouse is typically located within the sterile field.

The operating room also includes instrument cart 45 having tray 44 for holding a variety of surgical instruments and arrays 46. Instrument cart 45 and C-arm 26 are typically draped in sterile covers 48a, 48b to eliminate contamination risks within the sterile field.

The surgery is performed within the sterile field, adhering to the principles of asepsis by all scrubbed persons in the operating room. Patient 22 and physician 21 are prepared for the sterile field through appropriate scrubbing and clothing. The sterile field will typically extend from operating table 24 upward in the operating room. Typically both computer display image 38 and fluoroscope display image 28 are located outside of the sterile field.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with surgical navigation system 10 or by applying a statistical anatomical model. A morphed image of the patient's anatomy can be created by combining an image of the patient's anatomy with a data set, such as a virtual image of the patient's anatomy. Some imaging systems, such as C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3: C-Arm-Based Navigation, Springer-Verlag (2004).

Figure 2:
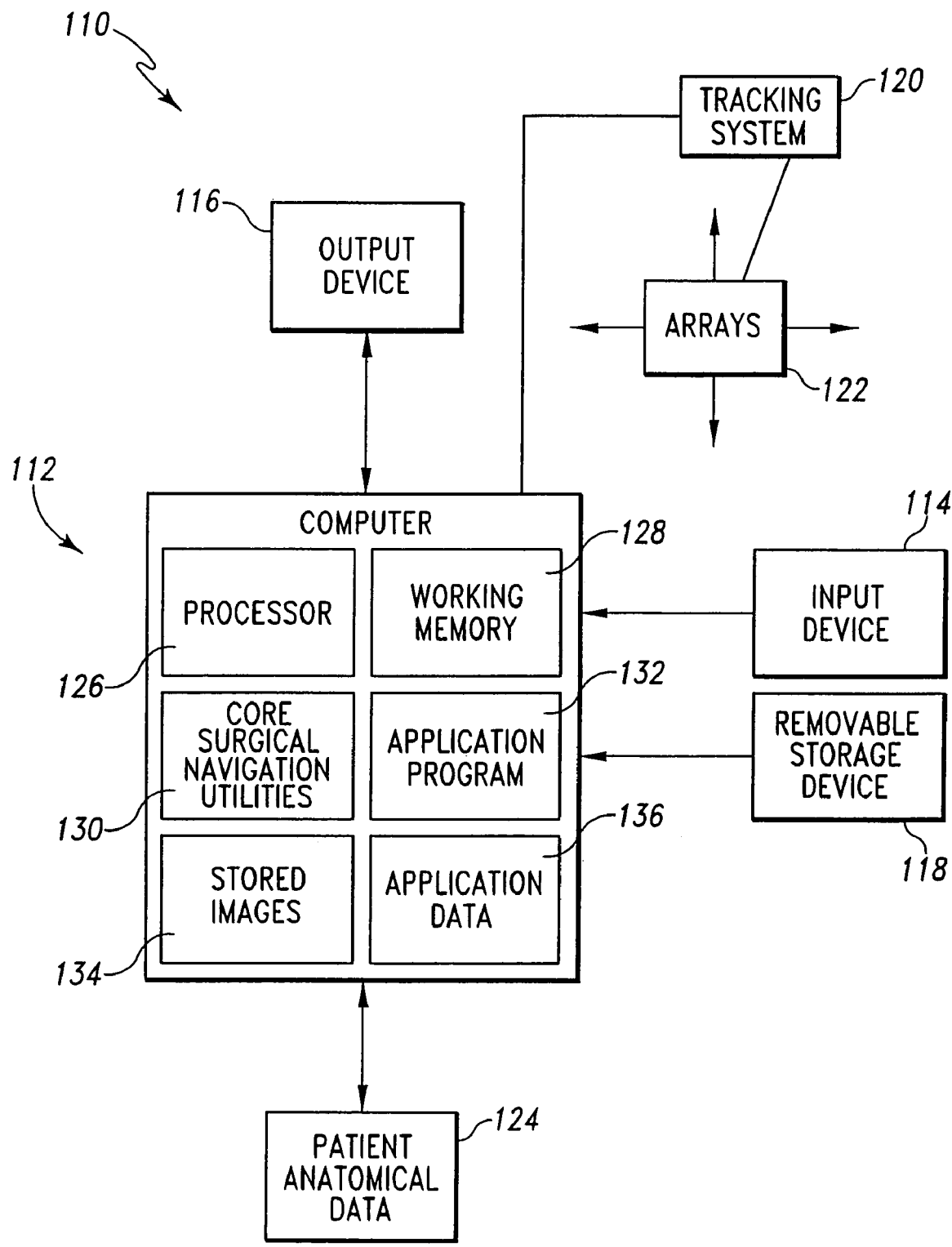
FIG. 2 is an exemplary block diagram of a surgical navigation system embodiment in accordance with the present teachings.

FIG. 2 is a block diagram of an exemplary surgical navigation system embodiment in accordance with the present teachings, such as an Acumen™ Surgical Navigation System, available from EBI, L.P., Parsippany, N.J. USA, a Biomet Company. The surgical navigation system 110 comprises computer 112, input device 114, output device 116, removable storage device 118, tracking system 120, arrays 122, and patient anatomical data 124, as further described in the brochure Acumen™ Surgical Navigation System, Understanding Surgical Navigation (2003) available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003), available from EBI, L.P. A more detailed description of an exemplary surgical navigation system is provided in James B. Stiehl et al., Navigation and Robotics in Total Joint and Spine Surgery, Chapter 1: Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises a processor 126, working memory 128, core surgical navigation utilities 130, an application program 132, stored images 134, and application data 136. Processor 126 is a processor of sufficient power for computer 112 to perform desired functions, such as one or more microprocessors. Working memory 128 is memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-knee"), total knee, hip, spine, trauma, intramedullary ("IM") nail/rod, and external fixator. Stored images 134 are those recorded during image acquisition using any of the imaging systems previously discussed. Application data 136 is data that is generated or used by application program 132, such as implant geometries, instrument geometries, surgical defaults, patient landmarks, and the like. Application data 136 can be pre-loaded in the software or input by the user during a surgical navigation procedure.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output.

Removable storage device 118 can be any device having a removable storage media that would allow downloading data, such as application data 136 and patient anatomical data 124. The removable storage device can be a read-write compact disc (CD) drive, a read-write digital video disc (DVD) drive, a flash solid-state memory port, a removable hard drive, a floppy disc drive, and the like.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood a measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of a passive tracking system is a Polaris® Passive System and an example of a marker is the NDI Passive Spheres™, both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System, available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This is accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122 can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). An array comprises a body and markers. The body comprises an area for spatial separation of the markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems.

Figure 3:
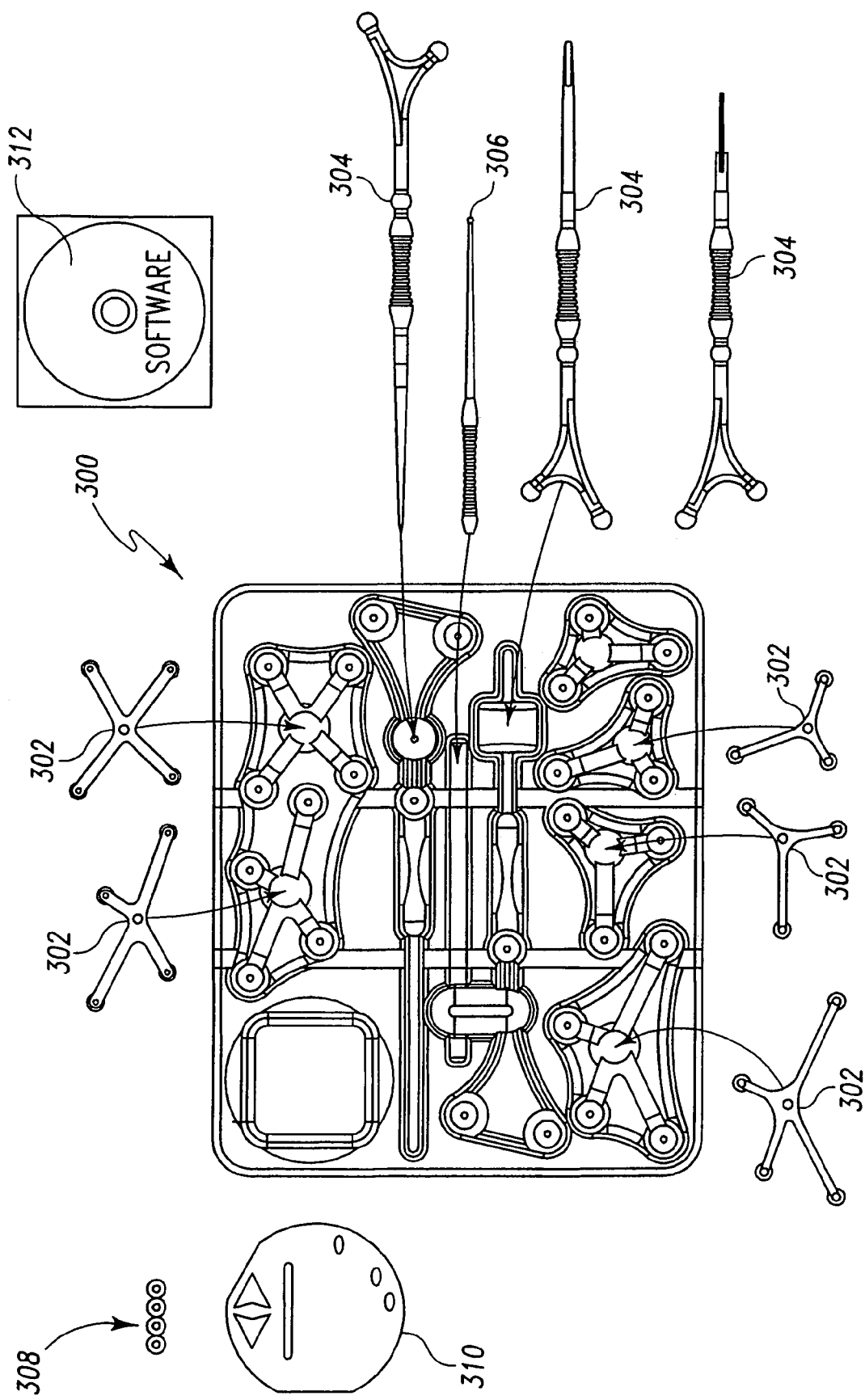
FIG. 3 is an exemplary surgical navigation kit embodiment in accordance with the present teachings.

FIG. 3 shows orthopedic application kit 300, which is used in accordance with the present teachings. Application kit 300 is typically carried in a sterile bubble pack and is configured for a specific surgery. Exemplary kit 300 comprises arrays 302, surgical probes 304, stylus 306, markers 308, virtual keypad template 310, and application program 312. Orthopedic application kits are available for unicondylar knee, total knee, total hip, spine, and external fixation from EBI, L.P.

Figure 4:
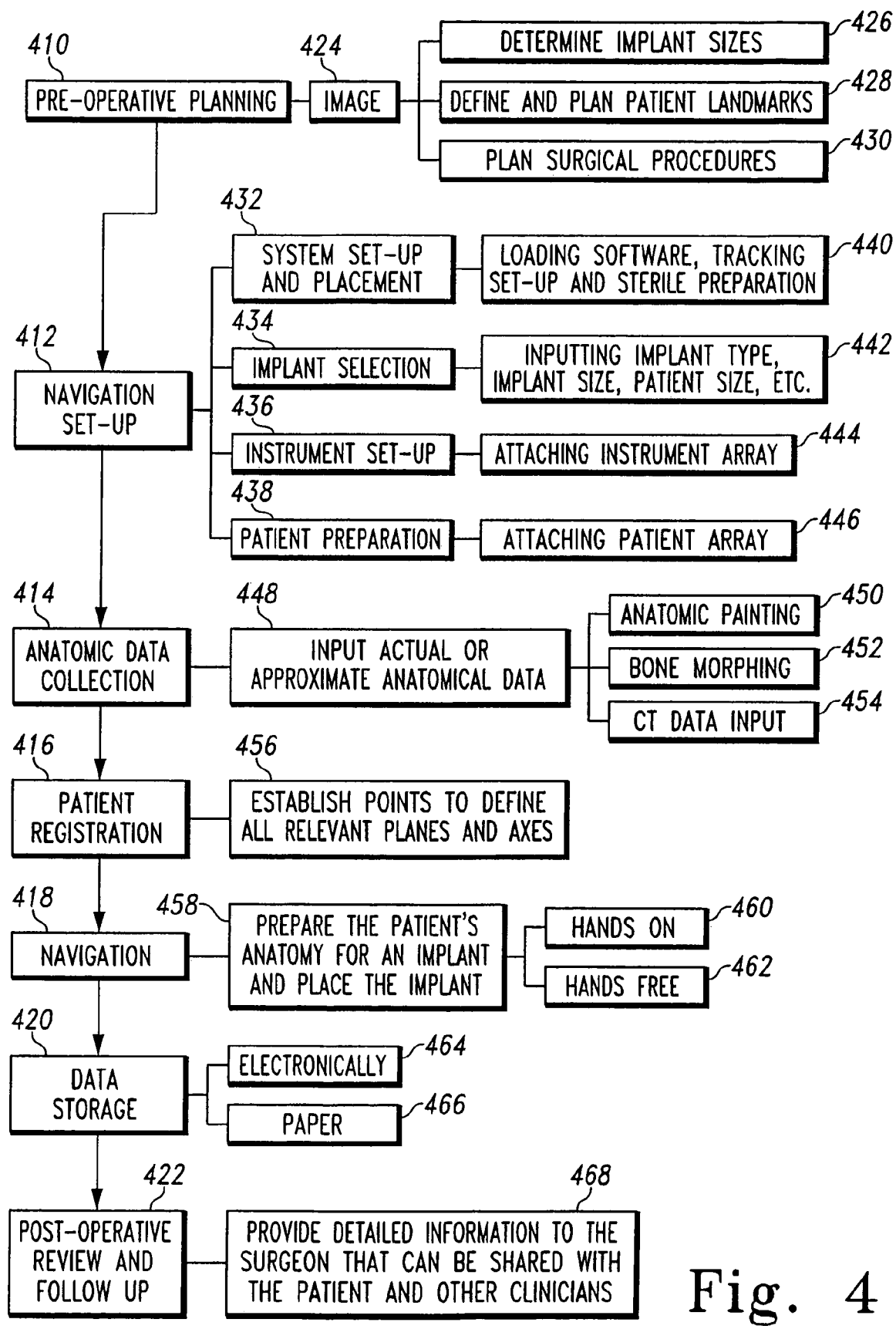
FIG. 4 is a flowchart illustrating the operation of an exemplary surgical navigation system in accordance with the present teachings.

FIG. 4 shows an exemplary illustration of surgical navigation system 10. The process of surgical navigation according to this exemplary embodiment includes pre-operative planning 410, navigation set-up 412, anatomic data collection 414, patient registration 416, navigation 418, data storage 420, and post-operative review and follow-up 422.

Pre-operative planning 410 is performed by generating an image 424, such as a CT scan that is imported into the computer. With image 424 of the patient's anatomy, the surgeon can then determine implant sizes 426, such as screw lengths, define and plan patient landmarks 428, such as long leg mechanical axis, and plan surgical procedures 430, such as bone resections and the like. Pre-operative planning 410 can reduce the length of intra-operative planning thus reducing overall operating room time.

Navigation set-up 412 includes the tasks of system set-up and placement 432, implant selection 434, instrument set-up 436, and patient preparation 438. System set-up and placement 432 includes loading software, tracking set-up, and sterile preparation 440. Software can be loaded from a pre-installed application residing in memory, a single use software disk, or from a remote location using connectivity such as the internet. A single use software disk contains an application that will be used for a specific patient and procedure that can be configured to time-out and become inoperative after a period of time to reduce the risk that the single use software will be used for someone other than the intended patient. The single use software disk can store information that is specific to a patient and procedure that can be reviewed at a later time. Tracking set-up involves connecting all cords and placement of the computer, camera, and imaging device in the operating room. Sterile preparation involves placing sterile plastic on selected parts of the surgical navigation system and imaging equipment just before the equipment is moved into a sterile environment, so the equipment can be used in the sterile field without contaminating the sterile field.

Navigation set-up 412 is completed with implant selection 434, instrument set-up 436, and patient preparation 438. Implant selection 434 involves inputting into the system information such as implant type, implant size, patient size, and the like 442. Instrument set-up 436 involves attaching an instrument array to each instrument intended to be used and then calibrating each instrument 444. Instrument arrays should be placed on instruments, so the instrument array can be acquired by the tracking system during the procedure. Patient preparation 438 is similar to instrument set-up because an array is typically rigidly attached to the patient's anatomy 446. Reference arrays do not require calibration but should be positioned so the reference array can be acquired by the tracking system during the procedure.

As mentioned above, anatomic data collection 414 involves a clinician inputting into the surgical navigation system actual or approximate anatomical data 448. Anatomical data can be obtained through techniques such as anatomic painting 450, bone morphing 452, CT data input 454, and other inputs, such as ultrasound and fluoroscope and other imaging systems. The navigation system can construct a bone model with the input data. The model can be a three-dimensional model or two-dimensional pictures that are coordinated in a three-dimensional space. Anatomical painting 450 allows a surgeon to collect multiple points in different areas of the exposed anatomy. The navigation system can use the set of points to construct an approximate three-dimensional model of the bone. The navigation system can use a CT scan done pre-operatively to construct an actual model of the bone. Fluoroscopy uses two-dimensional images of the actual bone that are coordinated in a three-dimensional space. The coordination allows the navigation system to accurately display the location of an instrument that is being tracked in two separate views. Image coordination is accomplished through a registration phantom that is placed on the image intensifier of the C-arm during the acquisition of images. The registration phantom is a tracked device that contains imbedded radio-opaque spheres. The spheres have varying diameters and reside on two separate planes. When an image is taken, the fluoroscope transfers the image to the navigation system. Included in each image are the imbedded spheres. Based on previous calibration, the navigation system is able to coordinate related anterior and posterior views and coordinate related medial and lateral views. The navigation system can also compensate for scaling differences in the images.

Patient registration 416 establishes points that are used by the navigation system to define all relevant planes and axes 456. Patient registration 416 can be performed by using a probe array to acquire points, placing a software marker on a stored image, or automatically by software identifying anatomical structures on an image or cloud of points. Once registration is complete, the surgeon can identify the position of tracked instruments relative to tracked bones during the surgery. The navigation system enables a surgeon to interactively reposition tracked instruments to match planned positions and trajectories and assists the surgeon in navigating the patient's anatomy.

During the procedure, step-by-step instructions for performing the surgery in the application program are provided by a navigation process. Navigation 418 is the process a surgeon uses in conjunction with a tracked instrument or other tracked array to precisely prepare the patient's anatomy for an implant and to place the implant 458. Navigation 418 can be performed hands-on 460 or hands-free 462. However navigation 418 is performed, there is usually some form of feedback provided to the clinician such as audio feedback or visual feedback or a combination of feedback forms. Positive feedback can be provided in instances such as when a desired point is reached, and negative feedback can be provided in instances such as when a surgeon has moved outside a predetermined parameter. Hands-free 462 navigation involves manipulating the software through gesture control, tool recognition, virtual keypad and the like. Hands-free 462 is done to avoid leaving the sterile field, so it may not be necessary to assign a clinician to operate the computer outside the sterile field.

Data storage 420 can be performed electronically 464 or on paper 466, so information used and developed during the process of surgical navigation can be stored. The stored information can be used for a wide variety of purposes such as monitoring patient recovery and potentially for future patient revisions. The stored data can also be used by institutions performing clinical studies.

Post-operative review and follow-up 422 is typically the final stage in a surgical procedure. As it relates to navigation, the surgeon now has detailed information that he can share with the patient or other clinicians 468.

Figure 5:
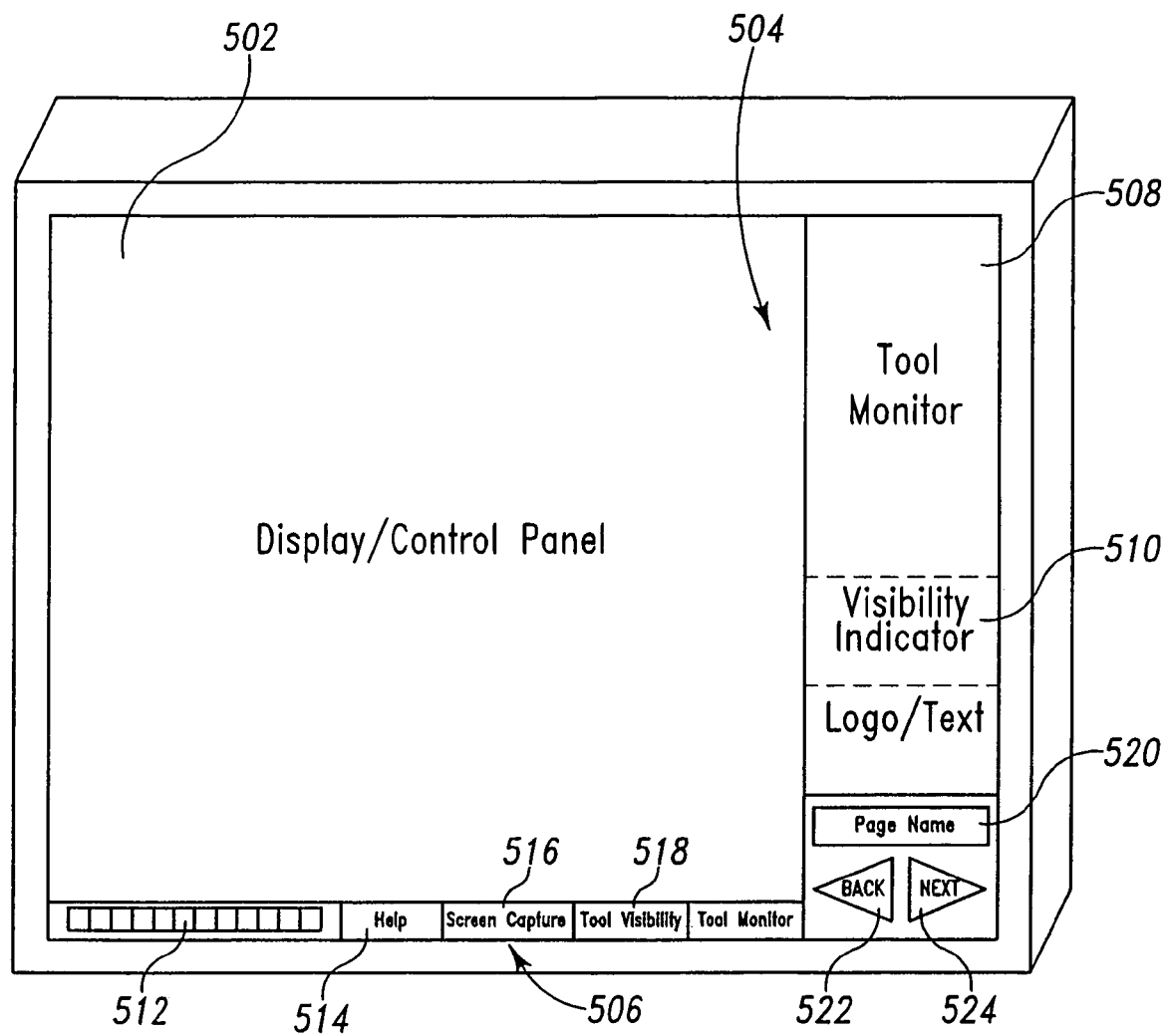
FIG. 5 shows a first exemplary computer display layout embodiment in accordance with the present teachings.

FIG. 5 shows a computer display layout embodiment in accordance with the present teachings. The display layout can be used as a guide to create common display topography for use with various embodiments of input devices 114 and to produce visual outputs at output device 116 for core surgical navigation utilities 130, application programs 132, stored images 134, and application data 136 embodiments. Each application program 132 is typically arranged into sequential pages of surgical protocol that are configured according to a graphic user interface scheme. The graphic user interface can be configured with a main display 502, a main control panel 504, and a tool bar 506. The main display 502 presents images such as selection buttons, image viewers, and the like. The main control panel 504 can be configured to provide information such as a tool monitor 508, visibility indicator 510, and the like. The tool bar 506 can be configured with a status indicator 512, help button 514, screen capture button 516, tool visibility button 518, current page button 520, back button 522, forward button 524, and the like. The status indicator 512 provides a visual indication that a task has been completed, visual indication that a task must be completed, and the like. The help button 514 initiates a pop-up window containing page instructions. The screen capture button 516 initiates a screen capture of the current page, and tracked elements will display when the screen capture is taken. The tool visibility button 518 initiates a visibility indicator pop-up window or adds a tri-planar tool monitor to the control panel 504 above the current page button 520. The current page button 520 can display the name of the current page and initiate a jump-to menu when pressed. The forward button 524 advances the application to the next page. The back button 522 returns the application to the previous page. The content in the pop-up will be different for each page.

Figure 6:
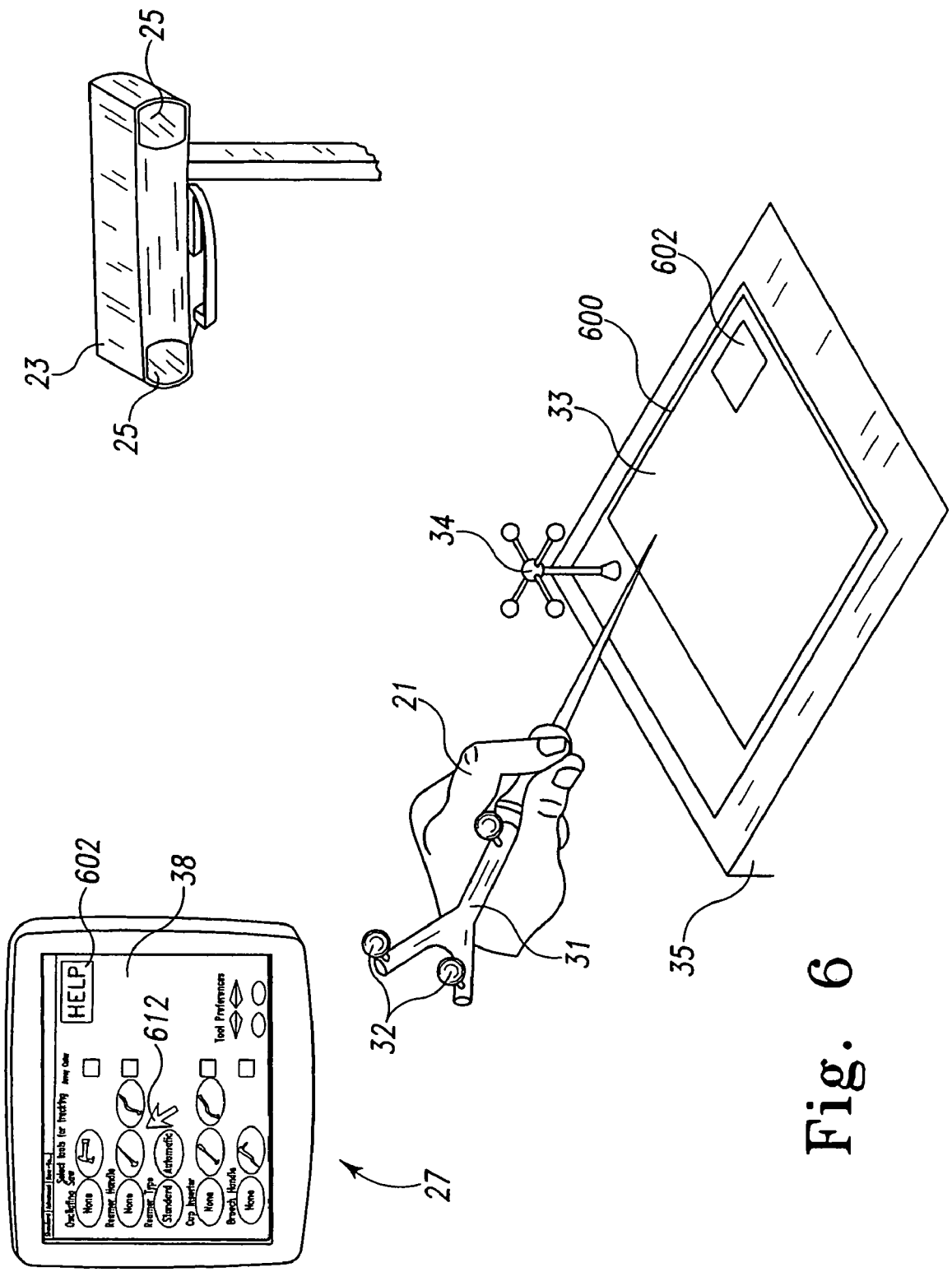
FIG. 6 is a fragmentary perspective view illustrating a virtual mouse and a method of using the virtual mouse in accordance with the present teachings.

FIG. 6 illustrates a fragmentary perspective view of a virtual mouse in accordance of the present teachings as used in, e.g., part of an image guided hip procedure. The virtual mouse includes probe 31, pad or "touch pad" 33 and pad array 34. The probe includes three reflective spheres 32 that form a probe array. It is common to those of skill in this art to refer to the combination of probe 31 and spheres 32 as a "probe array," and such reference is made occasionally herein. The touch pad includes a substantially flat surface as shown so that the tip of the probe can move along it, as described in further detail below.

Figure 7:
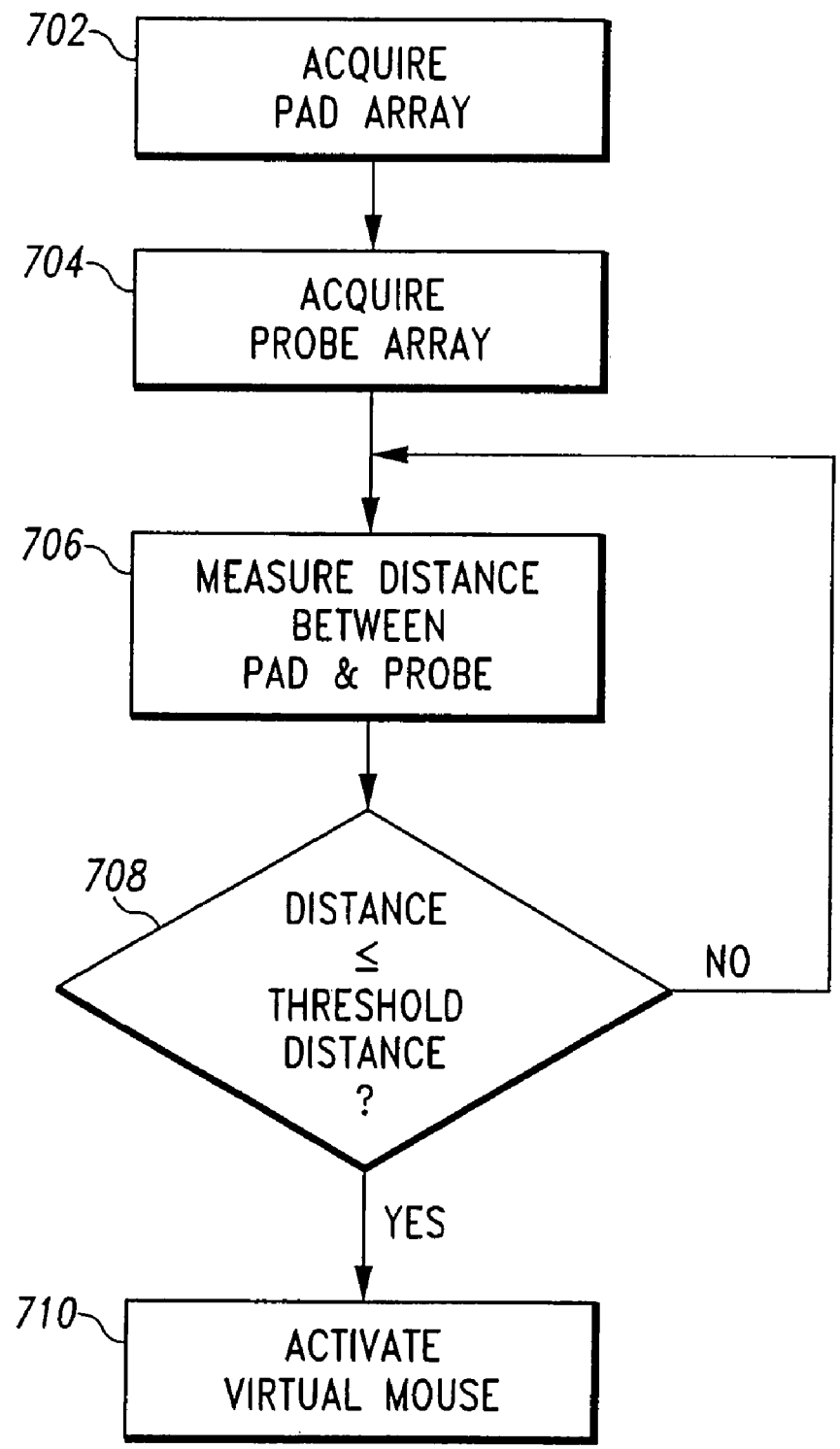
FIG. 7 is a block diagram illustrating the activation of a virtual mouse in accordance with the present teachings.

Activation of the virtual mouse is represented in the block diagram of FIG. 7. After the probe and touch pad are placed in the sterile field, surgical navigation system 10 must acquire them as shown in steps 702 and 704. These arrays are then tracked by the navigation system and the distance between them is calculated. Referring again to FIG. 6, the physician 21 points the probe 31 to the pad 33 that is supported by the table 35. The locating array 34 is used by the optical locator 23 to ascertain the location of the pad 33. By knowing the location of the pad 33 within the optical field, the location of the probe 31 can be tracked with respect to it. In the illustrated embodiment, the distance between the tip of probe 31 and the flat surface of touch pad 33 is determined, as depicted in step 706 of FIG. 7. The navigation system is programmed to activate the virtual mouse functionality when the probe 31 is positioned in close proximity to pad 33, as illustrated in blocks 708 and 710. The distance between the probe and pad at which the virtual mouse is activated is a design variable, but preferably is a few to several centimeters.

While physician 21 is preparing for or performing a surgery, the physician may select from a variety of icons shown in the computer display image 38 of the display 27 by using the virtual mouse functionality. Because the optical locator 23 senses the location of the probe 31 through use of the spheres 32, the location of the tip of the surgical probe 31 may also be determined. For instance, in FIG. 6, the tip of probe 31 is shown on display 38 as arrow 612 that is positioned close to the reamer handle icon. Those of skill in the art may interchangeably refer to arrow 612 as a "marker" or a "pointer," and occasional reference to these alternate terms is made herein. By moving probe 31 with respect to pad 33, physician 21 correspondingly makes a mouse input, namely, moving arrow 612 on display 38.

For purposes of this specification the terms "probe" and "probe array" should be construed broadly to include any known surgical devices capable of being used as a pointing instrument for activating or manipulating the exemplary virtual mouse devices of the present teachings. Examples of such devices include spatulas, hook probes and similar instruments. Whatever pointing device is used with the pad, it should have a tip and an array that allows it to be tracked by the navigation system.

The pad 33 can include a variety of indicia or "pad markers" to help the surgeon 21 navigate through the various icons on the computer display 38. For instance, the pad 33 can include a boundary or outline 600 which corresponds to a boundary or outline 600 of the computer display image 38. The boundary or outline 600 may be a visual indicator which is formed by paint, tape, or some other means of visual indication. The boundary 600 may also include a physical boundary such as a groove depression, or raised line such that the physician 21 may find the boundaries by touch when the probe crosses the physical features. In addition, the pad 33 also includes a help indicia 602, formed by either visual or physical indicators, such that the physician may select a help feature when desired. Furthermore, the pad may include indicia of a user interface screen.

While it is possible to include other indicia on the pad 33, typically only indicia corresponding to an icon on the computer display image which does not change from one image to another are displayed. It is within the scope of the teachings, however, to use a pad 33 which does not have any indicia including the boundary 600 or the help indicia 602. For instance, since the location of the probe 31 (determined by the markers 32) relative to the array 34, provides the required location data to the computer 12 to enable selection of the icons on the image 38.

Figure 8:
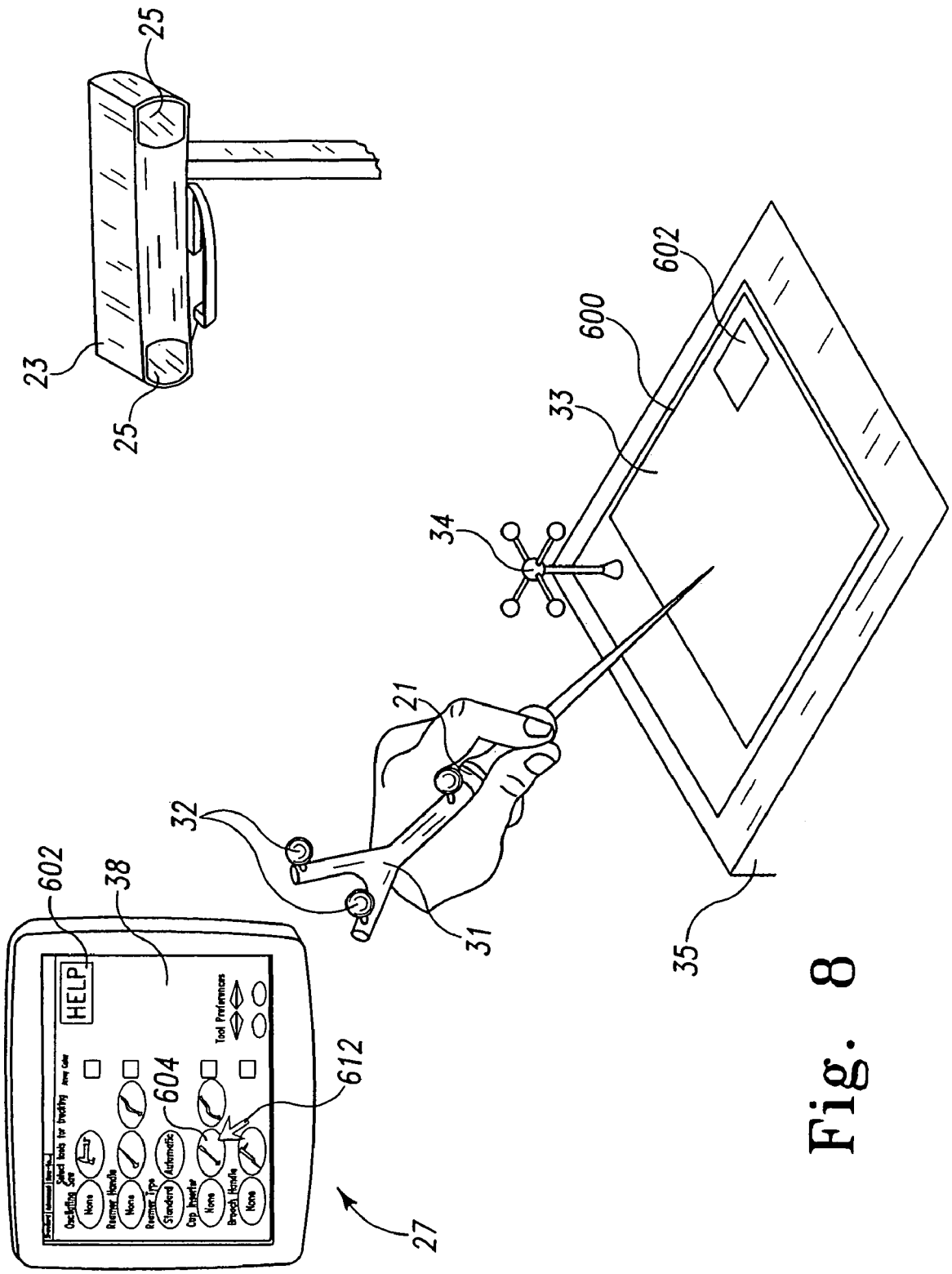
FIGS. 8-11 are fragmentary perspective views illustrating a virtual mouse and a method of using the virtual mouse in accordance with the present teachings.
Figure 9:
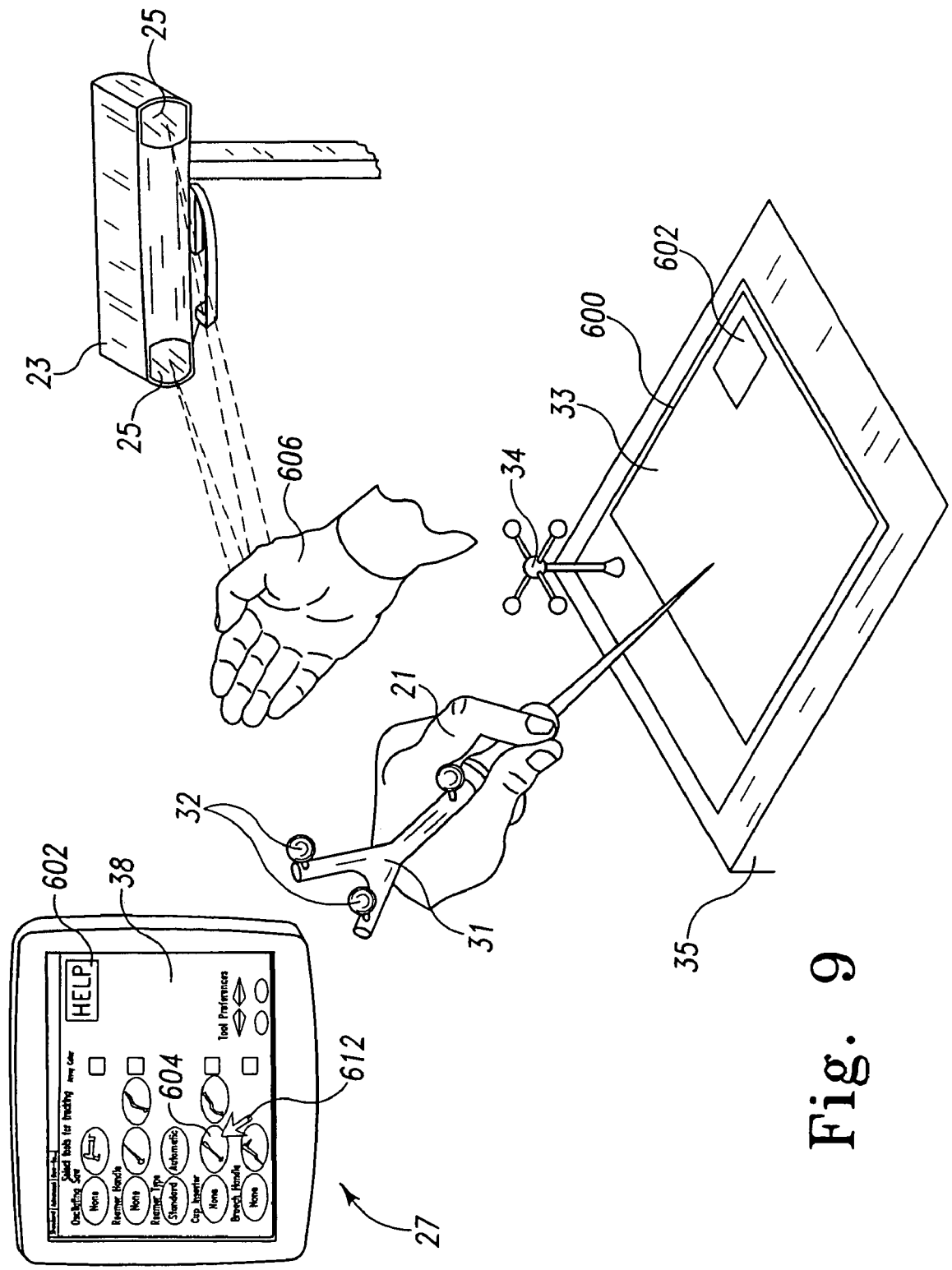

In FIG. 8, when the physician 21 has reached a point in the procedure where a cup inserter is required, the physician 21 moves the probe 31 to move pointer 612 to the icon 604 displayed on the computer display image 38. At this point in the procedure, the physician must select the icon 604 to move to the next page of the surgical protocol. To select the icon 604, the physician 21, as illustrated in FIG. 9, occludes or blocks the markers 32. The markers 32 may be occluded or blocked with the physician's free hand 606 or by other means. The break in the optical path between the markers 32 and cameras 25 is recognized by the computer 112. Once the markers are no longer sensed, the computer system indicates to the physician 21 that the icon 604 has been selected by changing the appearance of the icon. For instance, the color of the icon may be changed. It is also within the scope of the present teachings to indicate the selection of the icon 604 by other means or methods such as flashing the icon on and off or increasing the brightness of the icon 604. In addition, the screen 38 may include an indicator for the physician which provides information regarding how long the optical path should be blocked to select the icon 604. Once the physician decides to select the icon, the physician 21 removes his free hand 606 from the optical path. At this point, the computer system recognizes the re-establishment of the optical path to the markers 32 which causes the computer system to proceed to the next computer display image 38.

Figure 10:
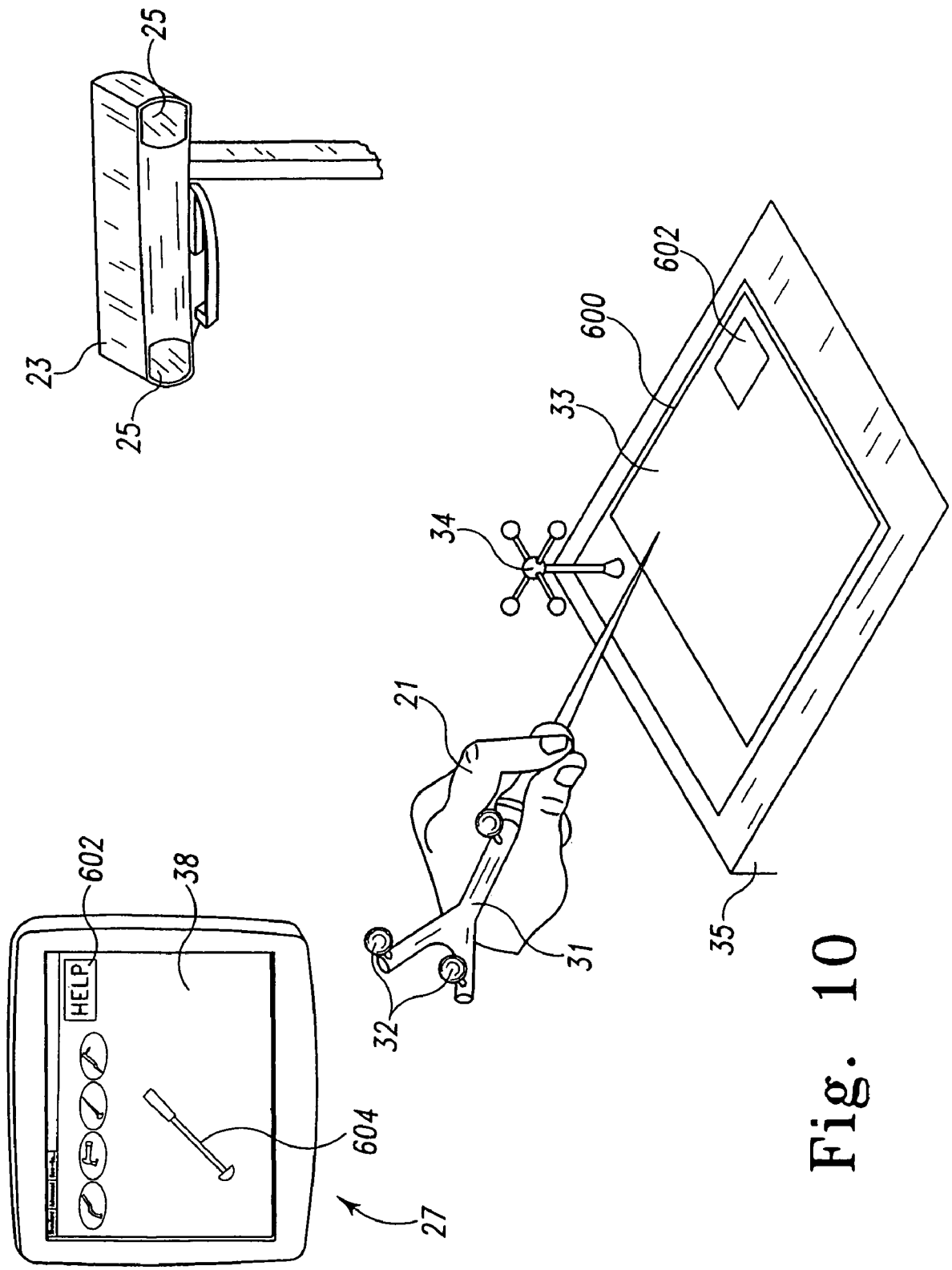

Referring now to FIG. 10, the next selected page of surgical protocol is shown which illustrates a more detailed display of the cup inserter 604. Once the cup inserter display 604 has been selected, the physician 21 can put down the surgical probe 31 and pick up the cup inserter so that the cup inserter may be appropriately identified or registered by the computer system.

As described with respect to FIG. 9, selective gesturing by occlusion of the optical path 606 makes a virtual mouse input, in this case, selecting an icon. As previously described, occluding the optical path for a certain period of time may be recognized by the computer as being equivalent to a click of a left mouse button on a conventional computer mouse. It is also within the scope of the present teachings to perform a double click on a button by occluding the optical path for a period of time, unblocking the optical path for a period of time, blocking the optical path again for a period of time and then unblocking the optical path. For a further description of selective gesturing, see Patent Application Ser. No. 60/693,461, titled "Selective Gesturing Input to a Surgical Navigation System" (hereinafter "Selective Gesturing application"), filed Jun. 23, 2005, which is incorporated by reference herein in its entirety.

Figure 11:
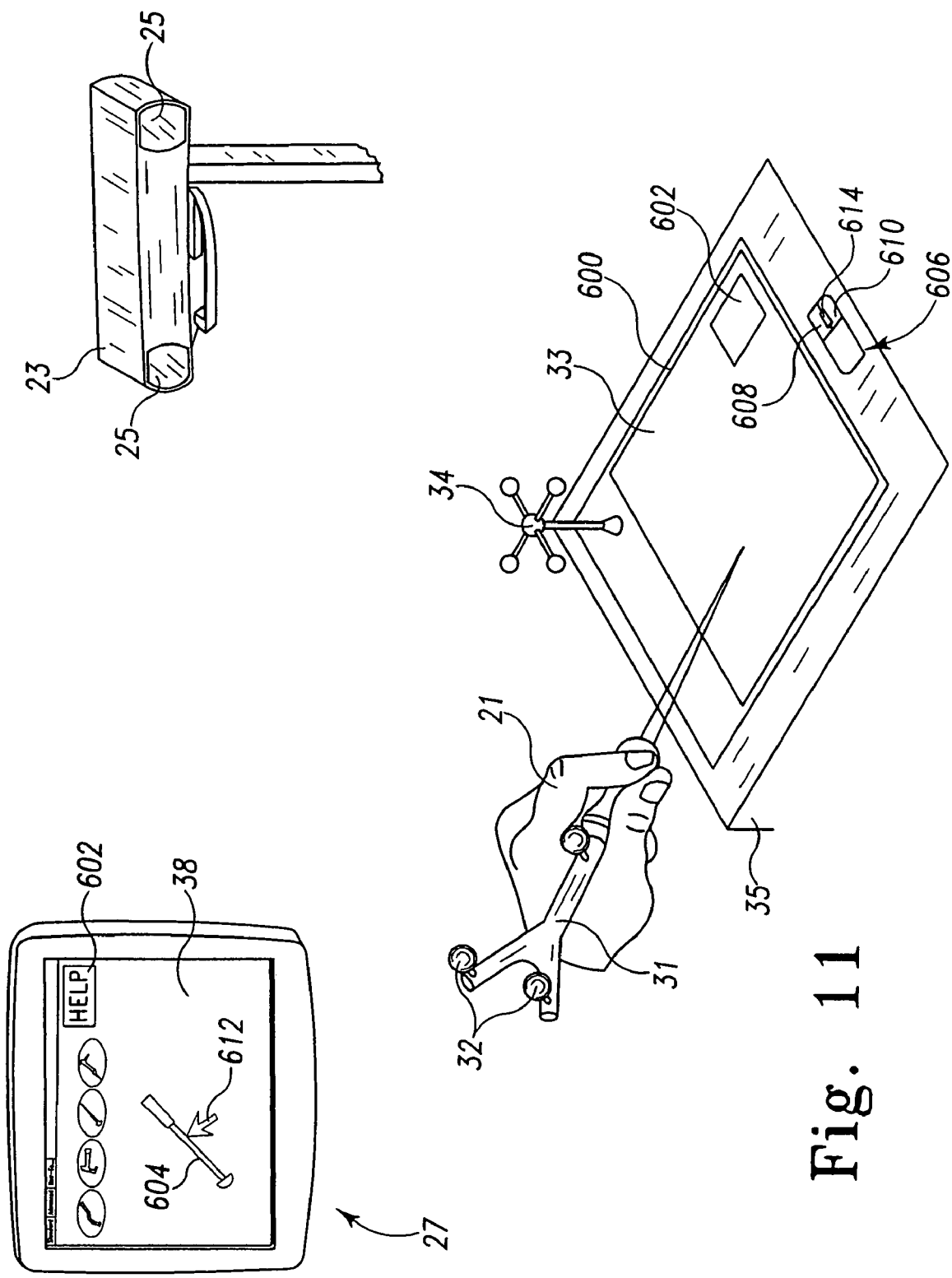

In a further embodiment, as illustrated in FIG. 11, the table 35 may include an image or replica of a mouse (or mouse) 606. It is also within the scope of the present teachings to include the image 606 within the boundary 600. The image 606 includes a left mouse button 608 and a right mouse button 610. To select the icon 604, the physician may move the probe 31 to point the pointer 612 to the icon 604 first, block the optical path to make a new selection, and then move the pointer 612 to the left mouse button 608 or right mouse button 610 to thereby use the known features of a mouse as is understood by those skilled in the art. For instance, selecting the mouse button 608 may be used to select an icon or a menu item. A double click or button 608 by using occlusion as previously described may provide for opening the next screen relating to an icon. Likewise, the right mouse button 610 may be used to bring up a menu of available selections. Consequently, it is within the scope of the present teachings to incorporate all of the known features of a mouse button or buttons including a selector wheel 614. Consequently, these teachings provide the function of a virtual mouse for enabling a physician 21 or technician to select various icons which are displayed on the display screen 38 and to move from one display screen to another without leaving the sterile field.

Figure 12:
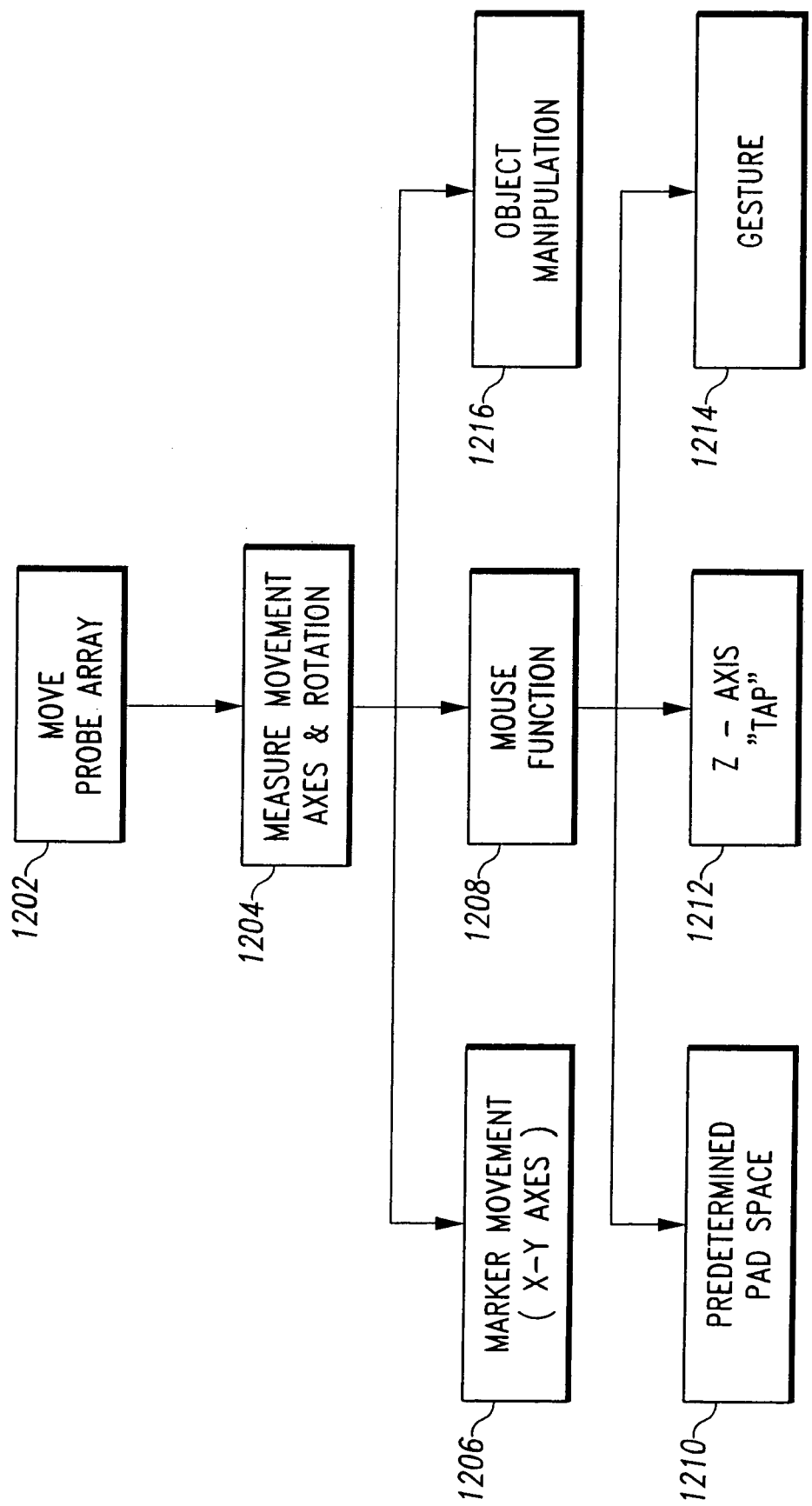
FIG. 12 is a block diagram which describes various features of embodiments incorporating the present teachings.

Having described a specific example employing the virtual mouse of the present teachings, a more generalized block diagram representing the virtual mouse functionality can be appreciated. As shown in FIG. 12, movement of probe array 31 (block 1202) is measured (block 1204). There are multiple types of movement that result in different mouse functionality or mouse inputs. For example, in block 1206, planar movement (x-y axes) of the probe along the surface of pad 33 is recognized by the system and correspondingly moves the arrow or marker on the screen, as described above. This is typically the mouse input that is used most.

Block 1208 represents mouse functionality that is further broken down in blocks 1210, 1212 and 1214 into "predetermined pad space," "z-axis" and "gesture," respectively. As described above with reference to FIG. 10, one example of a predetermined pad space is replica 606 that includes indicia of left and right mouse buttons and a scroll button. In these predetermined pad spaces (unlike the major surfaces of pad 33), the system recognizes movement of the probe as corresponding to a specific mouse function that is typically different than merely moving the arrow or marker on the monitor. For example, the predetermined space may include a pad marker indicia of a scroll dial, which, when the tip of the probe is moved along it, causes the monitor to scroll.

The system may also recognize and assign functionality to movement of the tip of the probe away from the surface of the pad, i.e., along the z-axis, as shown at block 1212. For example, a quick movement of the tip of the probe away from the pad a few centimeters and then returning the tip to substantially the same spot on the pad may be interpreted as equivalent to a single click of a conventional mouse. Similarly, two of these short "taps" may be interpreted as a double click. One of skill in the art would readily recognize many other functions or mouse inputs that could be assigned to various movements of the probe in the z-axis.

As described above with reference to FIG. 8, mouse functionality can be obtained through gesturing as indicated in block 1214. The gesturing can be interpreted by the system as equivalent to the click of a conventional mouse, or can be interpreted as other functions, such as equivalent to a "right click" of a conventional mouse. One of skill in the art would readily recognize many other functions that could be assigned to gesturing of the probe or pad arrays. A detailed description of selective gesturing is provided in the Selective Gesturing application incorporated by reference above.

These teachings also provide "object manipulation" capabilities (block 1216). For example, the tip of the probe may be moved across the flat surface of the pad, which causes corresponding movement of the pointer or arrow on the monitor, as described elsewhere. The arrow is moved until it is positioned over an image of human anatomy, such as a knee, for example. The probe may then be lifted from the flat surface of the pad, which is recognized by the computer as a mouse input triggering "object manipulation" mode. Once in this object manipulation mode, the computer translates three dimensional movement of the probe to corresponding three dimensional movement of the image on the monitor. While the exact correspondence between the three-dimensional movement of the probe and movement of the image is a design variable, it is preferable that the correspondence be intuitive. For example, rotating the probe along its long axis would rotate the image of the knee about the axis of the bone.

Figure 13:
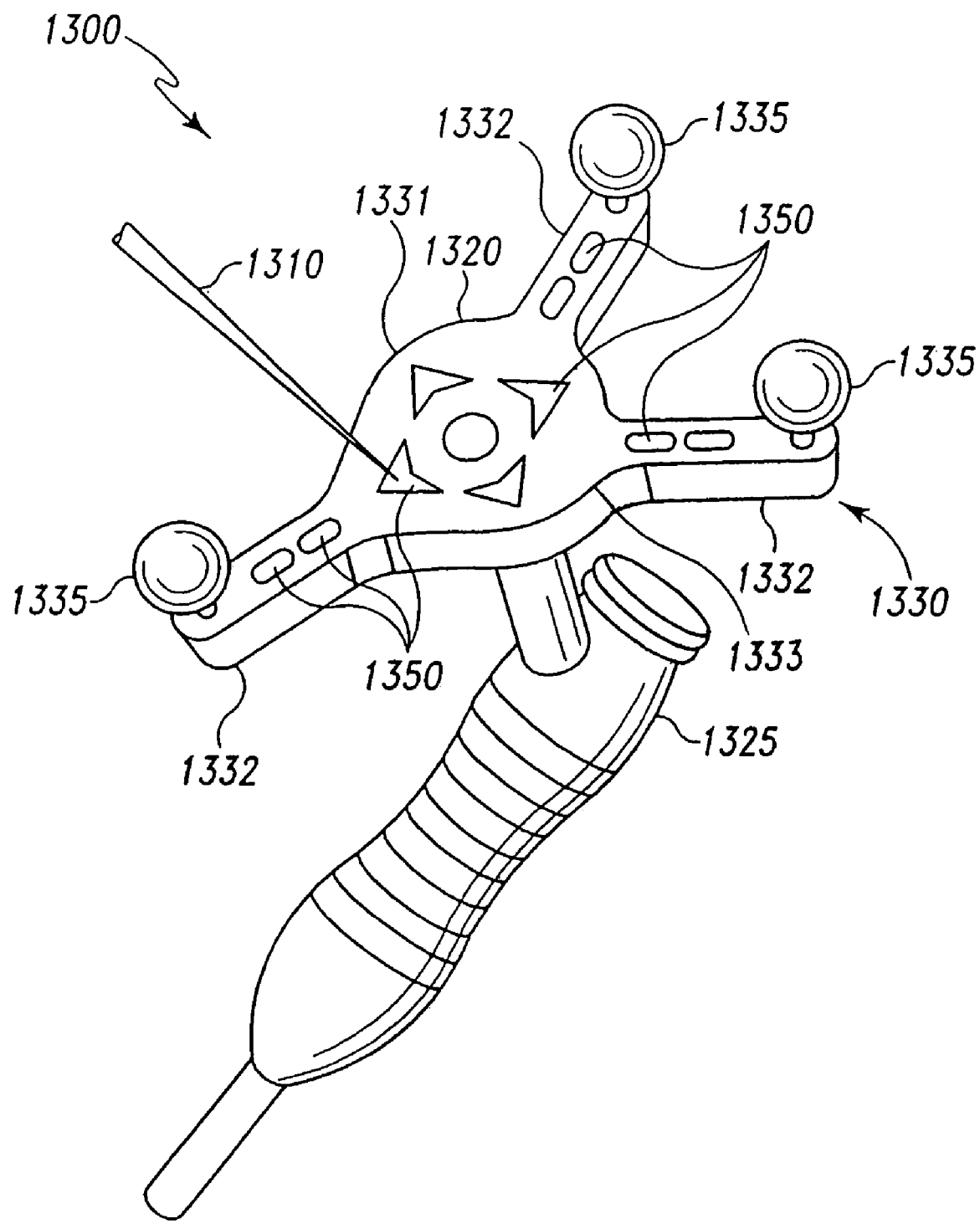
FIG. 13 is a fragmentary perspective view illustrating a virtual mouse in accordance with the present teachings.

In further exemplary embodiments, the touch pad or input pad portion of the virtual mouse device is located on the outer surface of a tracking array structure, such as an instrument array or a bone reference array. For instance, FIG. 13 illustrates a fragmentary perspective view of virtual mouse 1300 including probe 1310 (only the tip of the probe is shown) and input pad 1320, which is located on the top surface of tracking array 1330 (shown here as an instrument array attached to drill guide 1325). The tracking array 1330 includes a body 1331 and markers 1335. The body comprises a flat expanded area 1333 from which arms 1332 having markers 1335 extend. While three arms are shown in this illustration, those skilled in the art should understand and appreciate that in other exemplary embodiments the array structure can include two arms or even four or more arms. Area 1333 provides space on which a plurality of indicia or "pad markers" 1350 are included, each of which represent a unique functionality defined by the navigation system's software program. The pad markers are intuitively arranged on the surface of tracking array 1330 so that the surgeon can readily recognize them and can be represented by any number of input indicia, such as buttons for instance.

The geometric relationship between each of pad markers 1350 and surgical probe 1310 is known and stored in the navigation system's computer. Because of this known relationship, the computer is able to determine when surgical probe 1310 touches or is substantially near one of the pad markers and is able to translate this into a user input (e.g., a mouse input) to the computer that is coupled to the tracking system. For example, when the tip of tracked probe 1310 is positioned substantially near or brought into close proximity to one of the pad markers 1350, the computer's navigation software recognizes that the tip is near the marker and treats it as a mouse input to the computer. Each of the pad markers is assigned a specific functionality by the computer's software such that when the tip of the surgical probe is positioned near a given pad marker, the specific function assigned to that pad marker is performed. For instance, if one of the pad markers has been assigned the functionality of advancing the surgical protocol screen forward one page, when the tip of the probe is positioned substantially near this pad marker, the screen automatically advances forward one page.

Figure 14:
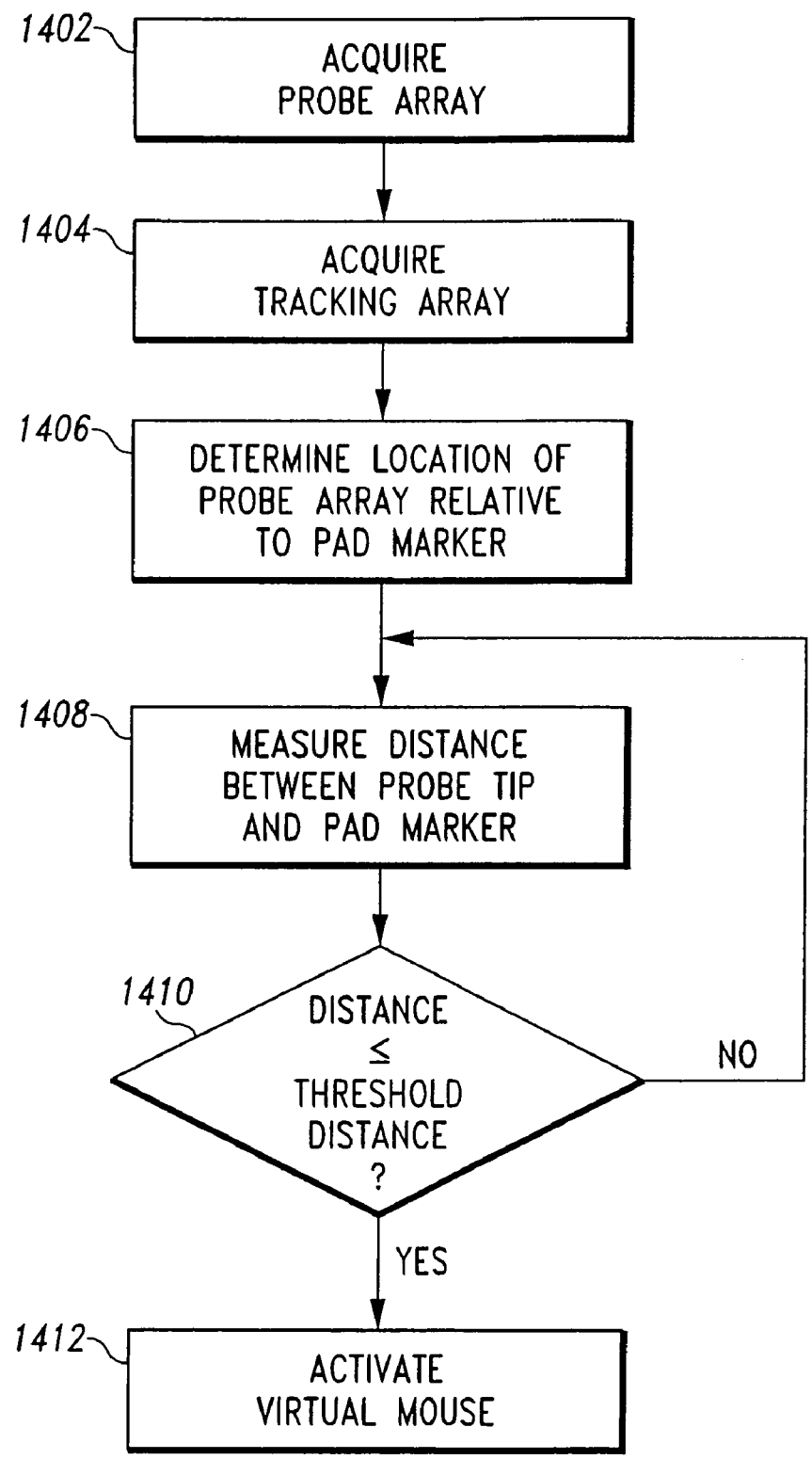
FIG. 14 is a block diagram illustrating the activation of a virtual mouse in accordance with the present teachings.

Activation of virtual mouse 1300 is represented in the block diagram of FIG. 14. After the probe array and tracking array are placed in the sterile field, the surgical navigation system 10 acquires them as shown in steps 1402 and 1404. These arrays are then tracked by the navigation system. As probe 1310 is positioned relative to one of pad markers 1350 on input pad 1320, the system determines this relationship by measuring the distance between the tip of the probe and the pad marker. Referring again to FIG. 13, physician 21 positions probe 1310 substantially at or near one of pad markers 1350 on input pad 1320. Tracking array 1330 is detected and recognized by the optical locator (not shown) to ascertain the location of pad 1320. By knowing the location of input pad 1320 within the optical field, the location of probe 1310 can be tracked with respect to it, and particularly where the tip of probe 1310 is located with respect to pad markers 1350 on the outer surface of tracking array 1330. In the illustrated embodiment, the distance between the tip of probe 1330 and one of pad markers 1350 on the tracking array is determined and measured, as depicted by steps 1406, 1408 of FIG. 14. The navigation system is programmed to activate the virtual mouse functionality when the probe 1310 is positioned in close proximity to one of pad markers 1350, as illustrated in blocks 1410 and 1412. The distance between the probe and pad marker on the pad array at which the virtual mouse is activated is a design variable, but preferably is a few to several centimeters.

Figure 15:
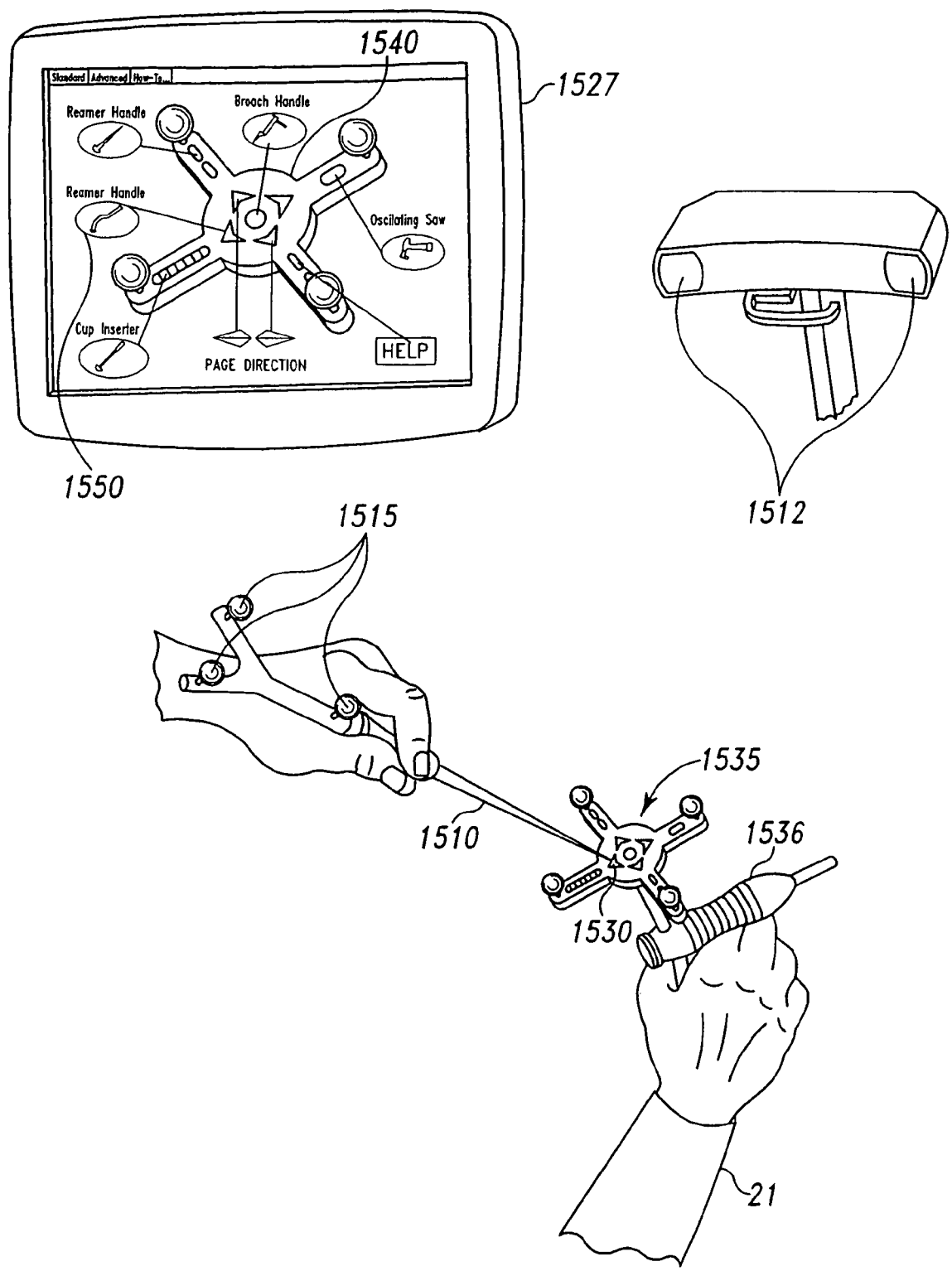
FIG. 15 is a fragmentary perspective view illustrating an exemplary virtual mouse and method of using the virtual mouse in accordance with the present teachings.
Figure 16:
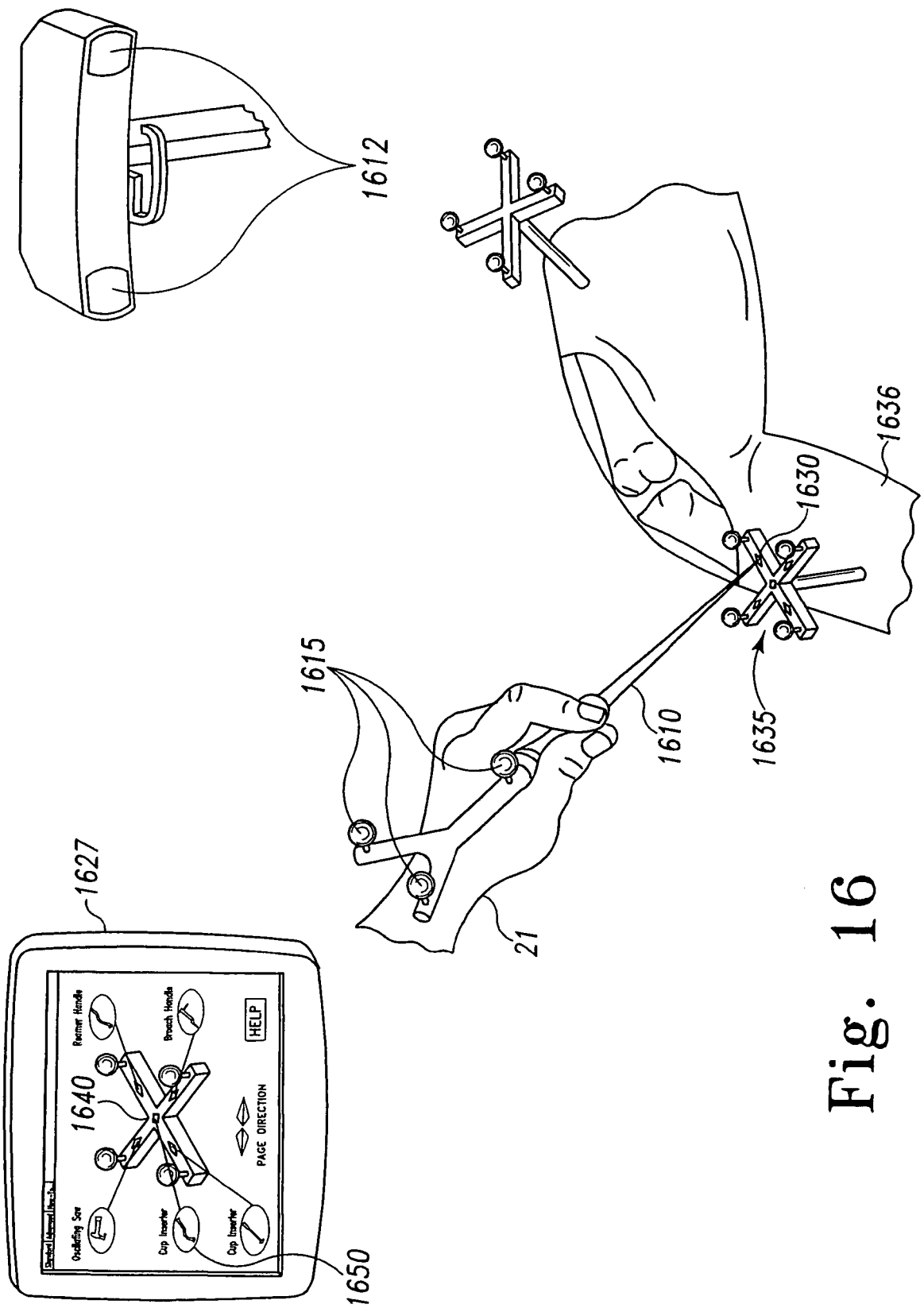
FIG. 16 is a fragmentary perspective view illustrating another exemplary virtual mouse and method of using the virtual mouse in accordance with the present teachings.

While physician 21 is preparing for or performing a surgery, the physician may select from a variety of icons displayed on a computer monitor by using the virtual mouse functionality. To accomplish this, system 10 is programmed to recognize a unique and/or select function for each of the pad markers on the tracking array. Because the optical locator is able to track the position of the probe's tip as it moves relative to the pad markers on the tracking array, the system is able to determine when the tip is positioned about or substantially near one of the pad markers. For instance, in FIGS. 15 and 16 the tip of probes 1510, 1610 is shown near pad marker 1530, 1630 of tracking arrays 1535, 1635, respectively (shown here as an instrument array on surgical drill guide 1536 in FIG. 15 and a bone reference array fixably attached to a patient's leg 1636 in FIG. 16). To determine the unique or select functionality of each pad marker, display monitors 1527, 1627 includes virtual representations 1540, 1640 of the tracking arrays 1535, 1635, which in turn define the functionality of each pad marker. For instance, pad markers 1530, 1630 each correspond to selecting icons 1550, 1650 for the reamer handle, as shown by the leading line connecting the pad marker on the virtual tracking array to its defined functionality. When physician 21 positions the tip of the probe 1510, 1610 substantially near pad markers 1530, 1630, respectively, a mouse input is sent to the computer system such that the icons 1550, 1650 are highlighted or identified as being chosen for selection by the surgeon as part of the surgical navigation procedure. At this point in the procedure, the surgeon must select the icon to move to the next page of the surgical protocol.

To select icons 1550, 1650, surgeon 21 must generate a second mouse input to the computer system. According to one exemplary embodiment, the surgeon can cause the second mouse input to the computer system by occluding or blocking the markers 1515, 1615 of the surgical probes 1510, 1610. The process of occluding a marker is discussed in detail above as well as specifically illustrated in FIG. 9. By breaking the optical path between markers 1515, 1615 and cameras 1512, 1612, the computer is able to interpret this action as a mouse input causing icons 1550, 1650 to be identified for selection. Once the surgeon decides to select the icons 1550, 1650, the surgeon can then remove his free hand from the optical path. At this point, the computer system recognizes the re-establishment of the optical path to the markers 1515, 1615, which in turn causes the computer system to proceed to the next step of the procedure.

In other exemplary embodiments, the second mouse input can be generated to the computer system by moving the tip of probes 1510, 1610 away from pad markers 1530, 1630, i.e., along the z-axis. For instance, a quick movement of the tip of probes 1510, 1610 away from pad markers 1530, 1630 a few centimeters and then returning the tip to substantially the same spot on the pad may be interpreted as equivalent to a single click of a conventional mouse. Similarly, two of these short "taps" may be interpreted as a double click. One of skill in the art would readily recognize many other functions or mouse inputs that could be assigned to various movements of the probe in the z-axis.

Figure 17:
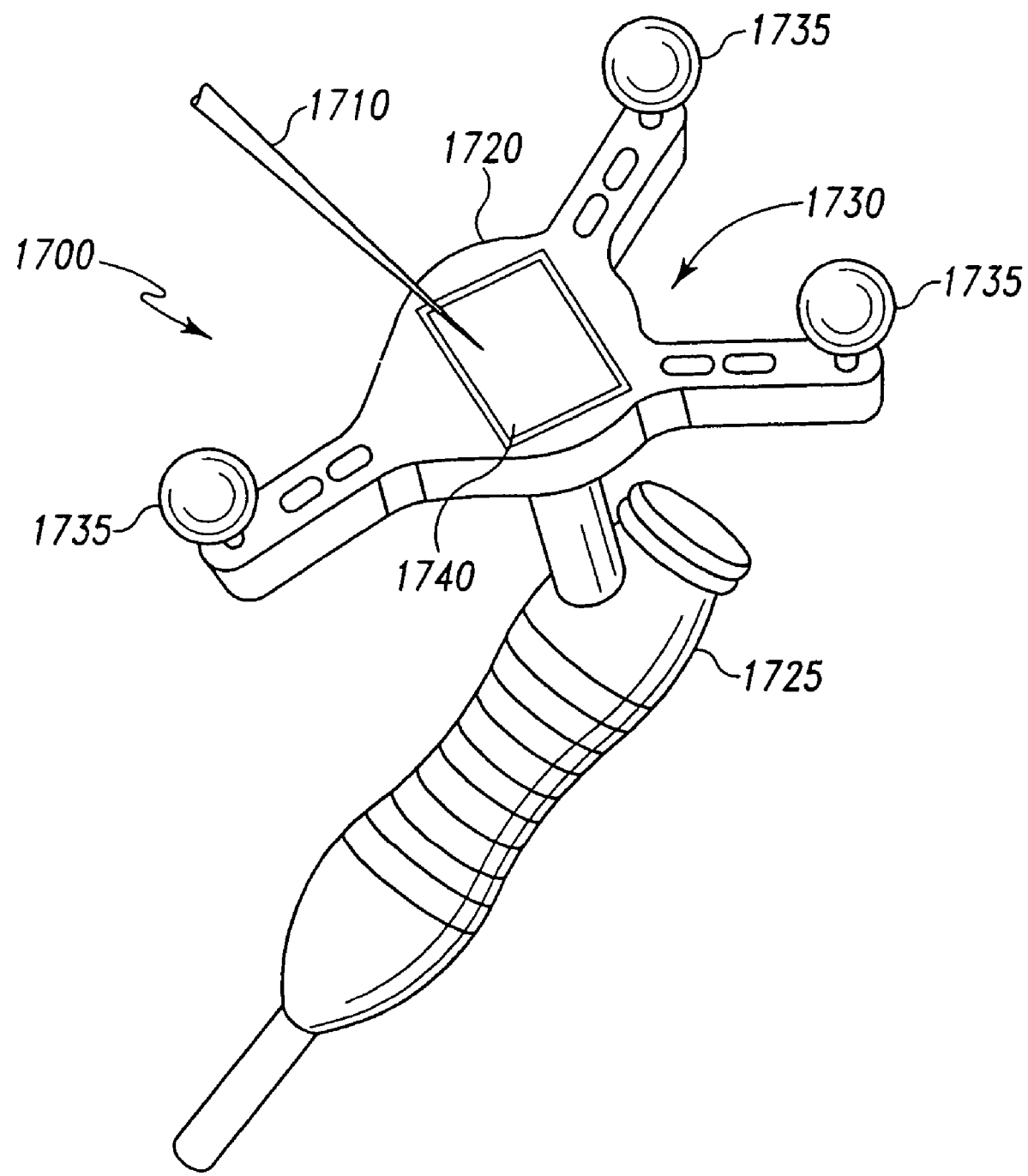
FIG. 17 is a fragmentary perspective view illustrating a further exemplary virtual mouse in accordance with the present teachings.

In addition to pad markers, the input pad may also comprise a substantially flat surface configured to cooperate with the tip of the surgical probe to cause the second mouse input to the computer. For instance, FIG. 17 illustrates a fragmentary perspective view of virtual mouse 1700 including probe 1710 (only the tip of the probe is shown) and input pad 1720, which is located on the top surface of tracking array 1730 (shown here as an instrument array attached to drill guide 1725). The substantially flat surface 1740 of input pad 1720 is configured such that the tip of probe 1710 can move along it, as is described in greater detail below. More particularly, physician 21 points the probe 1710 to input pad 1720, which is located between spheres 1735 of tracking array 1730. Tracking array 1730 is used by the optical locator to ascertain the location of input pad 1720. By knowing the location of input pad 1720 within the optical field, the location of probe 1710 can be tracked with respect to it. In the illustrated embodiment, the distance between the tip of probe 1710 and the flat surface 1740 of input pad 1720 is determined. As explained above, the navigation system is programmed to activate the virtual mouse functionality when probe 1710 is positioned in close proximity to input pad 1720.

Figure 18:
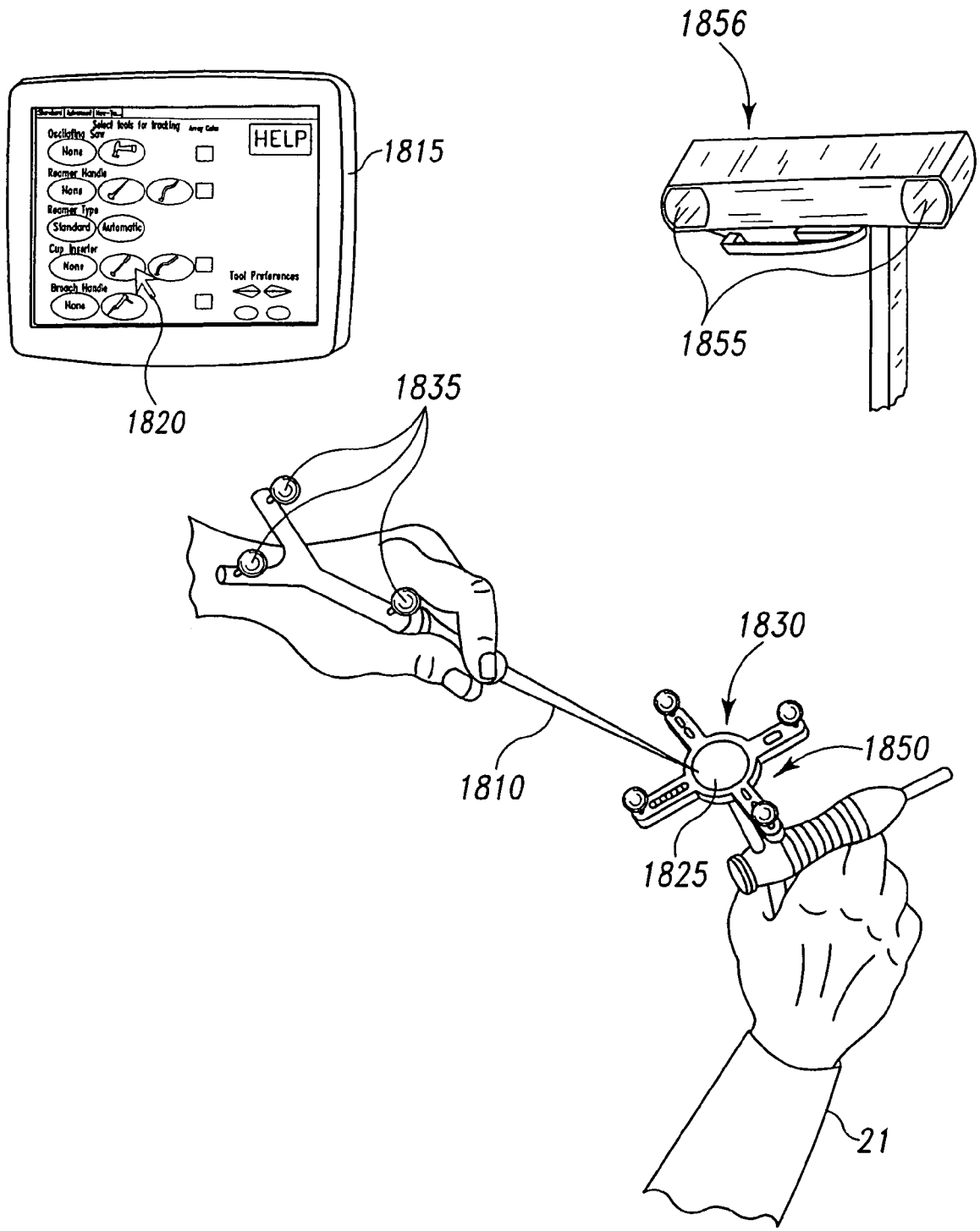
FIG. 18 is a fragmentary perspective view illustrating an exemplary virtual mouse and method of using the virtual mouse in accordance with the present teachings.

As explained in detail above, while the surgeon is preparing for or performing a surgery, a variety of icons displayed on the monitor may be identified and/or selected by using the virtual mouse functionality. More particularly, because cameras 1855 of optical locator 1856 sense the location of the probe through use of its trackable spheres, the location of the tip of the surgical probe may also be determined. For instance, in FIG. 18, the tip of probe 1810 is shown on display 1815 as arrow or pointer 1820 that is positioned close to the reamer handle icon. By moving probe 1810 with respect to input pad 1830, physician 21 correspondingly makes a mouse input, namely, moving arrow 1820 on display 1815.

When the physician 21 has reached a point in the procedure where an icon on the computer display 1815 requires selection in order to perform a desired function, the physician 21 moves the probe 1810 across the surface 1825 of the input pad 1830 on tracking array 1850 to correspondingly cause the arrow 1820 on the display 1815 to move. When the physician 21 positions the arrow 1820 over the desired icon, a mouse input is sent to the computer such that the icon is highlighted or identified as being chosen for selection by the surgeon. At this point in the procedure, the surgeon must select the icon to move to the next page of the surgical protocol. To select the icon, the physician 21, either occludes the markers 1835 of the probe 1810 or moves the tip of the probe 1810 away from the surface 1825 of the input pad 1830. Both of these procedures are discussed in great detail above and do not require further discussion here.

The virtual mouse input methods of the present teachings can also be embodied on a computer readable storage medium. According to these embodiments, the computer readable storage medium stores instructions that, when executed by a computer, cause the surgical navigation system to perform a virtual mouse input process. The computer readable storage medium can be any medium suitable for storing instruction that can be executed by a computer such as a compact disc (CD), digital video disc (DVD), flash solid-state memory, hard drive disc, floppy disc, and the like.

While an exemplary embodiment incorporating the principles of the present invention has been disclosed hereinabove, the present invention is not limited to the disclosed embodiments. Instead, this application is intended to cover any variations, uses, or adaptations of the invention using its general principles. For instance, instead of providing a pad, the present invention may include a stand marked appropriately and including an array 34. Further, this application is intended to cover such departures from the present disclosure as come within known or customary practice in the art to which this invention pertains and which fall within the limits of the appended claims.

What is claimed is:

1. A method of performing a surgery, comprising:
   providing a surgical navigation system having a tracking system, computer and monitor placed outside of a sterile field;
   placing a tracking array into the sterile field, the tracking array including a frame and being attachable to a surgical instrument being used by a surgeon to perform the surgery or a bone, wherein the frame of the tracking array has an input pad disposed on its outer surface;
   placing a probe having a probe array within the sterile field;
   acquiring the tracking array and the probe array with the tracking system;
   activating a virtual mouse by positioning the probe relative to the input pad; and
   causing a mouse input to the computer with the virtual mouse.

2. The method of claim 1, wherein activating the virtual mouse with the probe comprises positioning a tip of the probe substantially near a pad marker located on the input pad to cause the mouse input.

3. The method of claim 2, wherein the mouse input comprises identifying a function on the monitor with a pointer.

4. The method of claim 3, further comprising moving the tip of the probe away from the pad marker to cause a second mouse input.

5. The method of claim 4, wherein the second mouse input comprises selecting the function on the monitor.

6. The method of claim 3, further comprising occluding the probe array to cause a second mouse input.

7. The method of claim 6, wherein the second mouse input comprises selecting the function on the monitor.

8. The method of claim 1, wherein activating the virtual mouse with the probe comprises moving the probe substantially near the input pad to cause a pointer on the monitor to correspondingly move.

9. The method of claim 1, wherein activating the virtual mouse with the probe comprises moving a tip of the probe along a substantially flat surface of the input pad to cause the mouse input.

10. The method of claim 9, wherein the mouse input comprises moving a pointer to correspondingly position a cursor on the monitor over an icon.

11. The method of claim 10, further comprising moving the tip of the probe away from the pad marker to cause a second mouse input.

12. The method of claim 11, wherein the second mouse input comprises selecting the function displayed by the monitor.

13. The method of claim 10, further comprising occluding the probe array to cause a second mouse input.

14. The method of claim 13, wherein the second mouse input comprises selecting the function displayed by the monitor.

15. The method of claim 1, further comprising moving the probe away from the input pad to manipulate a corresponding object on the computer monitor, the corresponding object being a human anatomy image.

16. A surgical navigation system, comprising:
    a computer having a monitor and surgical navigation utilities software;
    a tracking system coupled to the computer and establishing a measurement field;
    a tracking array recognizable by the tracking system when exposed to the measurement field, the tracking array including a frame and being attachable to a surgical instrument being used by a surgeon to perform the surgery or a bone;
    an input pad disposed on an outer surface of the frame; and
    a probe having a probe array recognizable by the tracking system when exposed to the measurement field;
    wherein the software comprises a program that when executed causes the system to recognize positioning of the probe relative to the input pad as a mouse input.

17. The surgical navigation system of claim 16, wherein the input pad comprises a pad array associated therewith.

18. The surgical navigation system of claim 16, further comprising a pad marker located on the input pad, the pad marker configured to cooperate with the probe during use of the system to cause the mouse input.

19. The surgical navigation system of claim 18, wherein movement of the probe's tip near the pad marker during operation of the system causes the mouse input.

20. The surgical navigation system of claim 19, wherein movement of the probe's tip away from the pad marker during operation of the system causes a second mouse input.

21. The surgical navigation system of claim 19, wherein occlusion of the probe array from exposure to the measurement field during operation of the system causes a second mouse input.

22. The surgical navigation system of claim 16, wherein the input pad has a substantially flat surface and the probe has a tip, movement of which along the substantially flat surface during operation of the system causes the mouse input.

23. The surgical navigation system of claim 22, wherein movement of the tip away from the surface causes a second mouse input.

24. The surgical navigation system of claim 22, wherein occlusion of the probe array from exposure to the measurement field causes a second mouse input.

25. The surgical navigation system of claim 16, wherein the tracking array comprises an instrument array or a bone reference array.

* * * * *